(12) United States Patent
Morishita

(10) Patent No.: US 9,797,852 B2
(45) Date of Patent: Oct. 24, 2017

(54) APPLIED VOLTAGE CONTROL DEVICE FOR SENSOR

(71) Applicant: DENSO CORPORATION, Kariya, Aichi-pref. (JP)

(72) Inventor: Koji Morishita, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/150,562

(22) Filed: May 10, 2016

(65) Prior Publication Data

US 2016/0363551 A1    Dec. 15, 2016

(30) Foreign Application Priority Data

Jun. 12, 2015  (JP) ................. 2015-119307

(51) Int. Cl.
| | | |
|---|---|---|
| *G01N 27/02* | (2006.01) | |
| *G01N 27/04* | (2006.01) | |
| *G01D 3/036* | (2006.01) | |
| *G01N 33/00* | (2006.01) | |
| *G01R 27/02* | (2006.01) | |

(52) U.S. Cl.
CPC ......... *G01N 27/028* (2013.01); *G01D 3/0365* (2013.01); *G01N 27/04* (2013.01); *G01N 33/0036* (2013.01); *G01R 27/02* (2013.01)

(58) Field of Classification Search
CPC .. G01N 27/028; G01N 27/04; G01N 33/0036; G01R 27/02
See application file for complete search history.

(56) References Cited

U.S. PATENT DOCUMENTS

| | | | | |
|---|---|---|---|---|
| 5,461,902 A | * | 10/1995 | Iwata ................. | F02D 41/1494 73/23.32 |
| 5,547,552 A | * | 8/1996 | Hasegawa .......... | G01N 27/4065 204/401 |
| 2008/0178856 A1 | * | 7/2008 | Adams ................ | F02D 41/1494 123/697 |
| 2008/0196480 A1 | * | 8/2008 | Kawase ............. | G01N 27/4065 73/31.05 |

FOREIGN PATENT DOCUMENTS

JP    2000-065781 A    3/2000

* cited by examiner

*Primary Examiner* — Jermele M Hollington
*Assistant Examiner* — Zannatul Ferdous
(74) *Attorney, Agent, or Firm* — Posz Law Group, PLC

(57) ABSTRACT

An applied voltage control device is used for a sensor, in which a direct current corresponding to an oxygen amount flows when a DC voltage is applied to the sensor, and an alternating current corresponding to a sensor impedance flows when an AC voltage is applied to the sensor. The applied voltage control device includes: a filtering unit that sets a cutoff frequency of the AC voltage applied to the sensor variable.

12 Claims, 14 Drawing Sheets

FIG. 5A E/G STATE
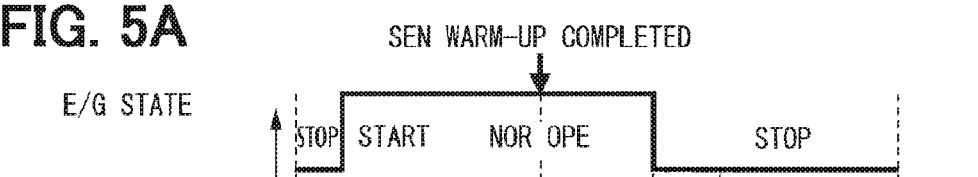
FIG. 5B SEN TEMP
FIG. 5C CUT-OFF-SW
FIG. 5D CUT-OFF FREQ
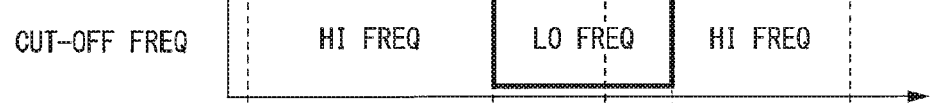
FIG. 5E AC V APP WAVEFORM
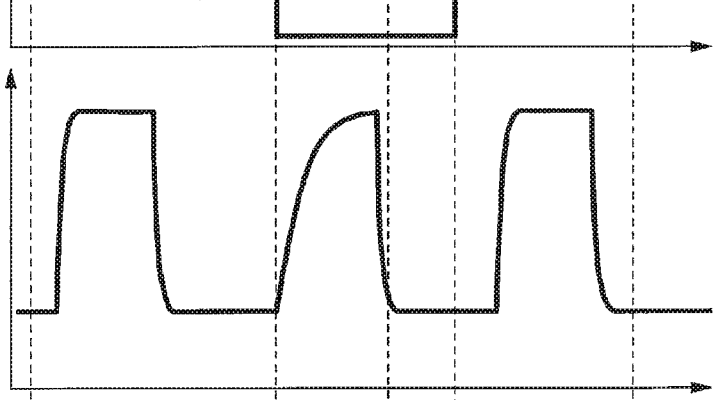
FIG. 5F SEN IMPEDANCE Zac
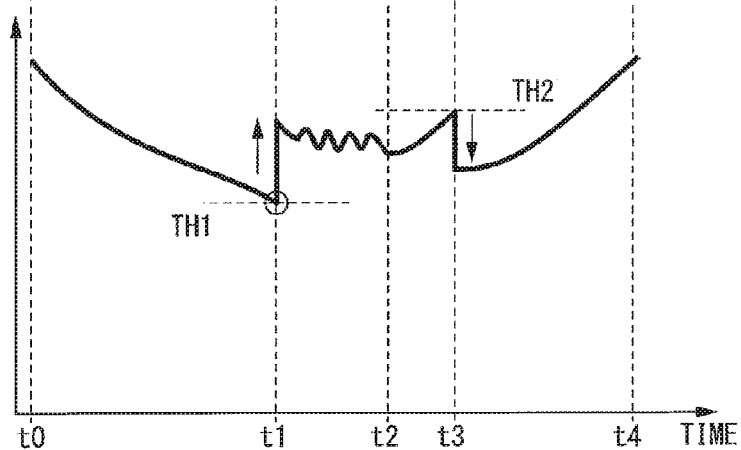

FIG. 7A E/G STATE
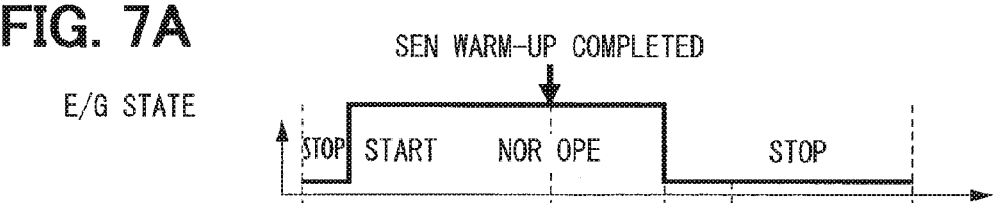
FIG. 7B SEN TEMP
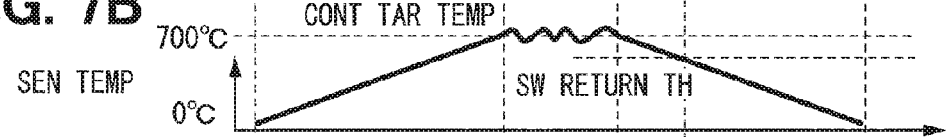
FIG. 7C CUT-OFF-SW
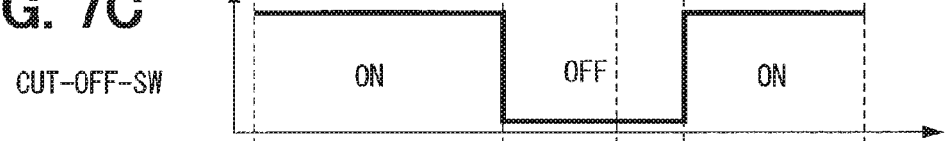
FIG. 7D CUT-OFF FREQ
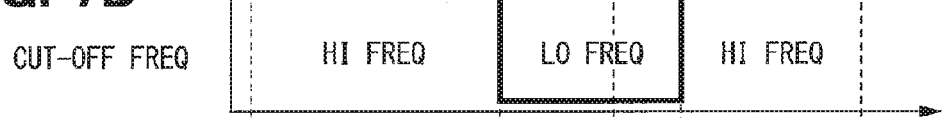
FIG. 7E AC V APP WAVEFORM
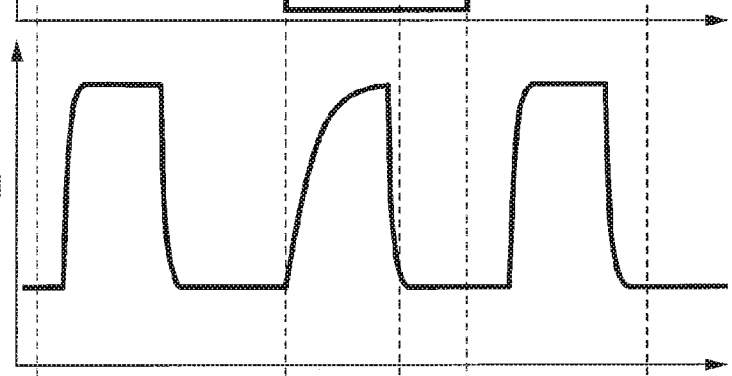
FIG. 7F SEN OUT CUR Iac
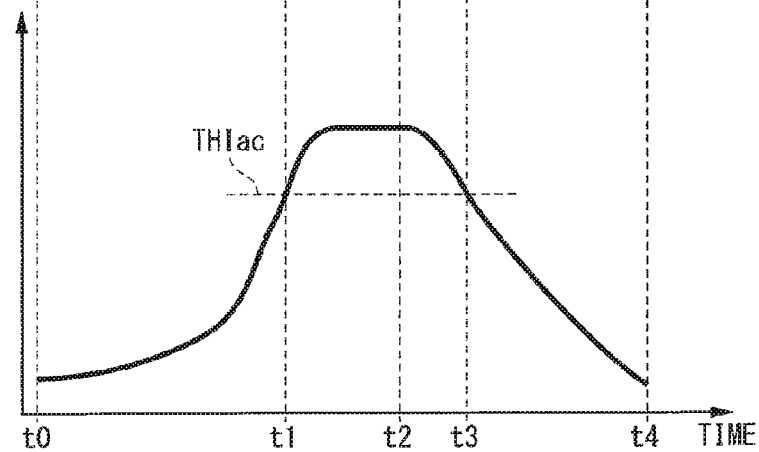

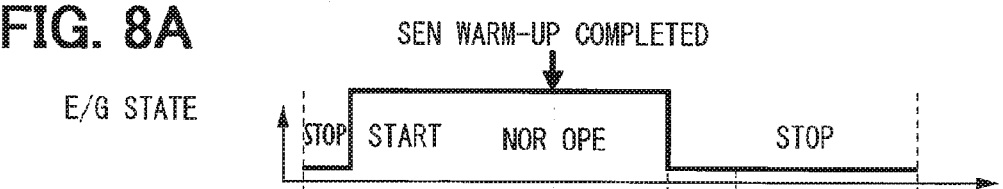
FIG. 8A E/G STATE
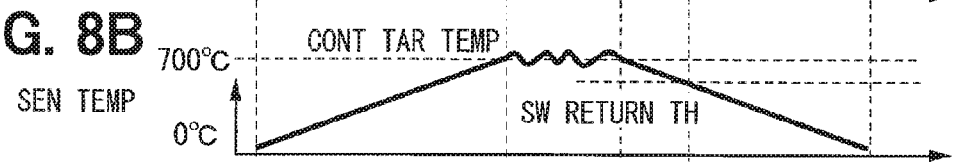
FIG. 8B SEN TEMP
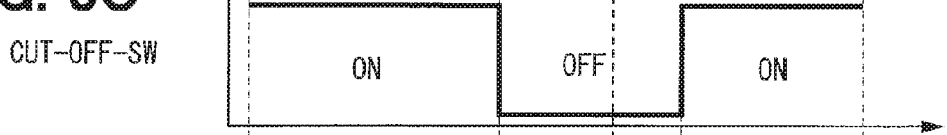
FIG. 8C CUT-OFF-SW
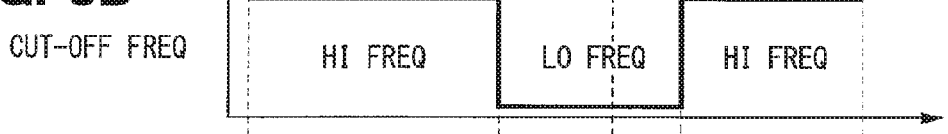
FIG. 8D CUT-OFF FREQ
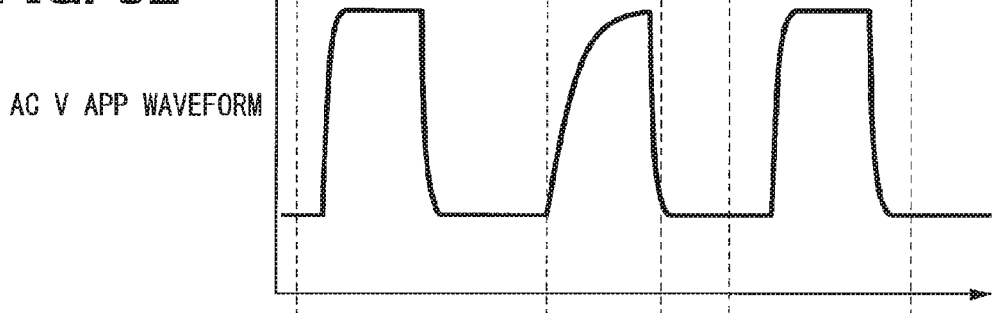
FIG. 8E AC V APP WAVEFORM
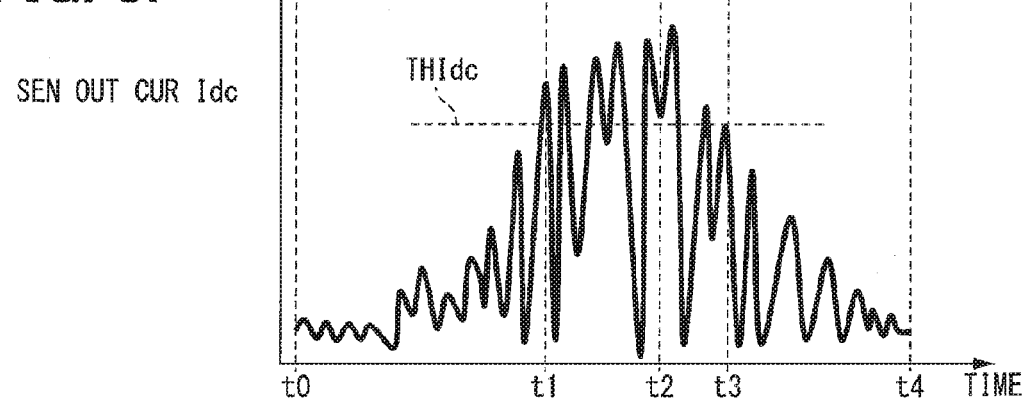
FIG. 8F SEN OUT CUR Idc

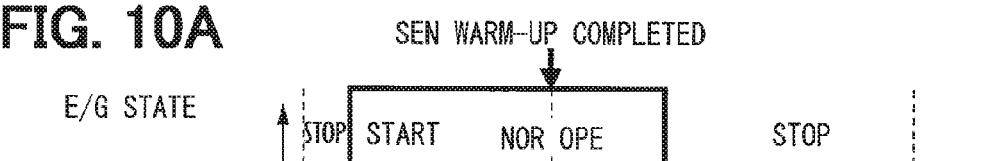
FIG. 10A E/G STATE
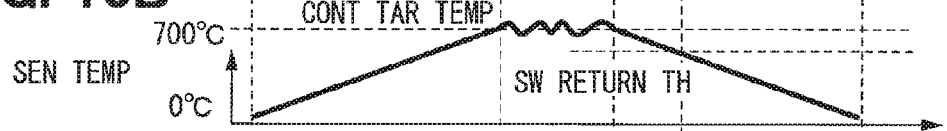
FIG. 10B SEN TEMP
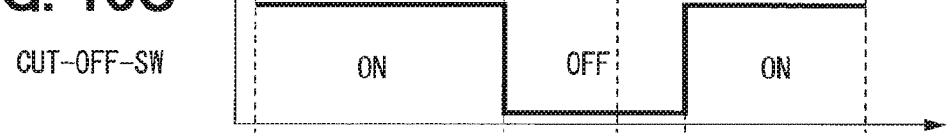
FIG. 10C CUT-OFF-SW
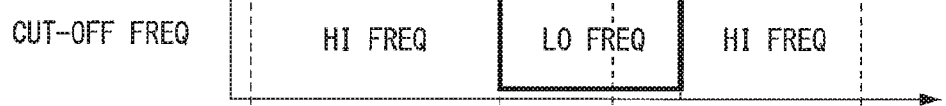
FIG. 10D CUT-OFF FREQ
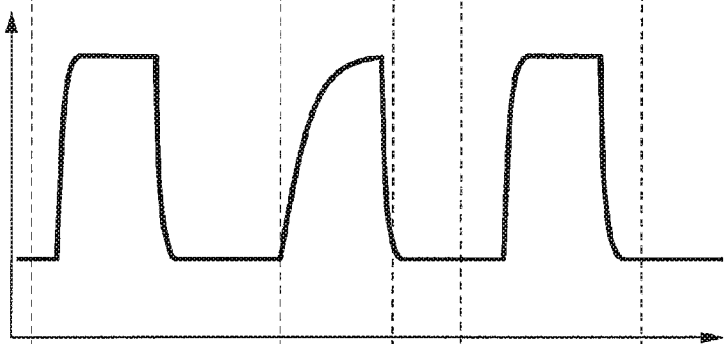
FIG. 10E AC V APP WAVEFORM
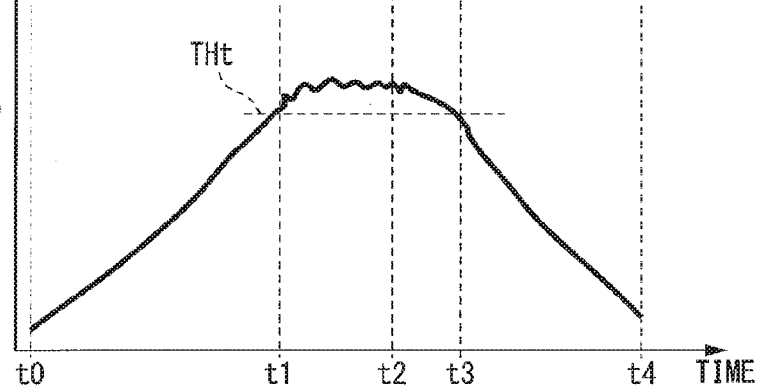
FIG. 10F EXHAUST GAS TEMP Te FIG. 12A E/G STATE
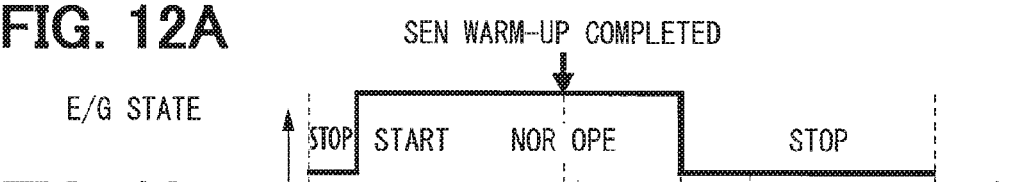
FIG. 12B SEN TEMP
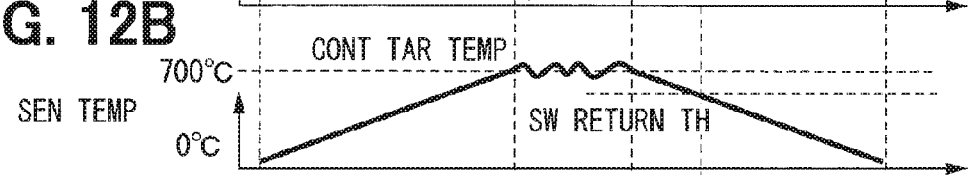
FIG. 12C CUT-OFF-SW
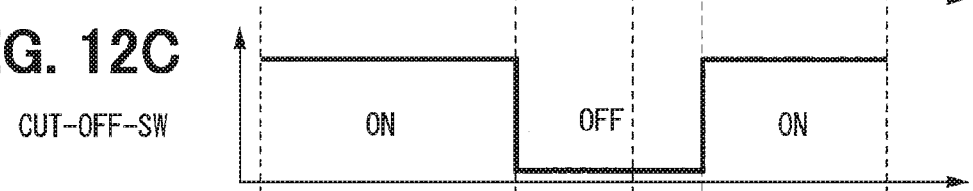
FIG. 12D CUT-OFF FREQ
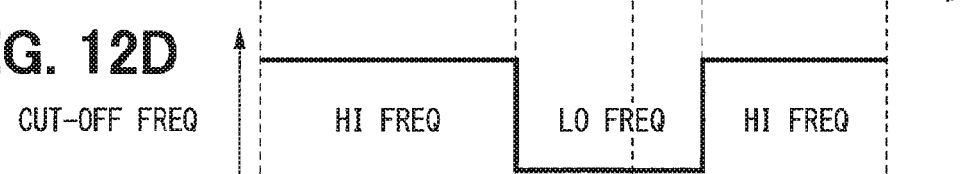
FIG. 12E AC V APP WAVEFORM
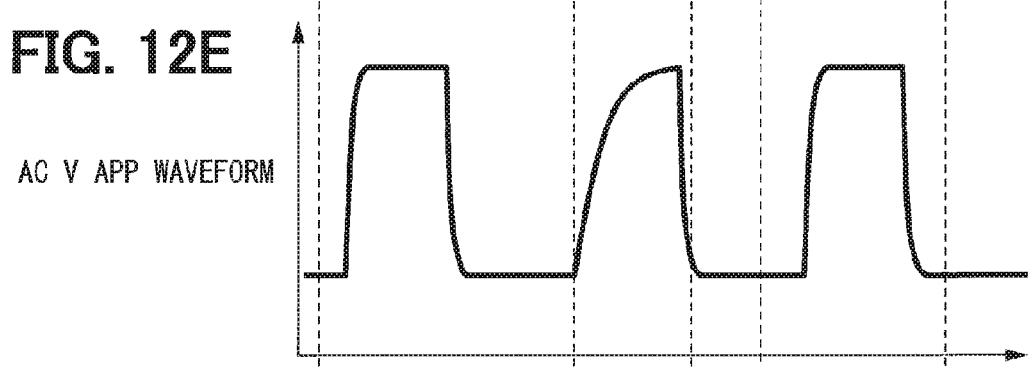
FIG. 12F HEATER CUR Ih
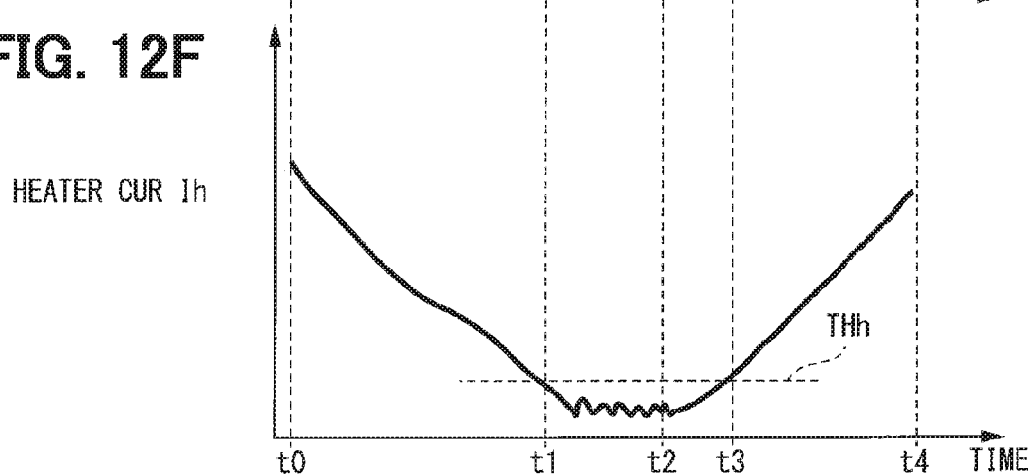

FIG. 14A E/G STATE
SEN WARM-UP COMPLETED
STOP | START | NOR OPE
FIG. 14B SEN TEMP
CONT TAR TEMP
700°C
0°C
FIG. 14C CUT-OFF-SW
ON | OFF
FIG. 14D CUT-OFF FREQ
HI FREQ | LO FREQ
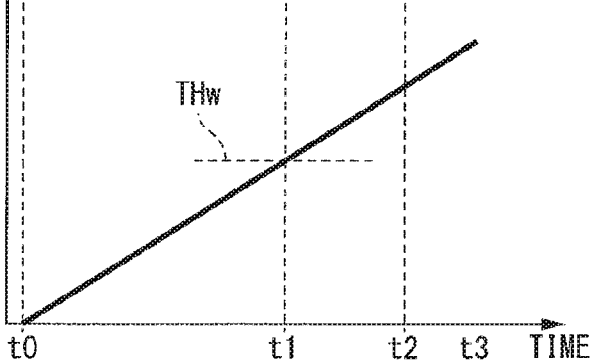
FIG. 14E AC V APP WAVEFORM
FIG. 14F SEN HEAT P Wr
THw
t0  t1  t2  t3  TIME

APPLIED VOLTAGE CONTROL DEVICE FOR SENSOR

CROSS REFERENCE TO RELATED APPLICATION

This application is based on Japanese Patent Application No. 2015-119307 filed on Jun. 12, 2015, the disclosure of which is incorporated herein by reference.

TECHNICAL FIELD

The present disclosure relates to an applied voltage control device for a sensor that allows a current corresponding to an oxygen amount to flow therethrough by the application of a voltage.

BACKGROUND

Conventionally, there has been known a sensor that has the characteristic of allowing a current corresponding to an oxygen amount to flow therethrough by the application of a DC voltage and is capable of detecting the oxygen amount on the basis of a value of the output current such as an oxygen content sensor or an air-fuel ratio sensor. Generally, such a sensor has a large temperature dependence, and output thereof thus varies depending on an element temperature. Thus, it is necessary to maintain the element temperature at an appropriate temperature (active temperature) in order to maintain an excellent accuracy of oxygen amount detection. Thus, there is a system that includes a heater attached to a sensor, and feedback-controls energization to the heater so as to maintain the element temperature at an active temperature by heat generation of the heater (refer to Patent Literature 1, for example).

In this system, it is necessary to detect the element temperature to feedback-control the energization to the heater. However, disposing a temperature sensor which directly measures the element temperature on the above sensor may result in upsizing of the sensor and a cost increase. In view of this, there has been proposed a method that estimates an element temperature of a sensor on the basis of information other than the element temperature. For example, Patent Literature 1 describes a method that detects a sensor AC current $\Delta I$ generated from an AC voltage $\Delta V$ applied to an oxygen content sensor, calculates an AC impedance $Z(=\Delta V/\Delta I)$ or an admittance $Y(=1/Z=\Delta I/\Delta V)$ of the sensor, and estimates an element temperature of the oxygen content sensor on the basis of the impedance Z or the admittance Y. Patent Literature 1 also describes switching performed in such a manner that the impedance Z is calculated to use the temperature estimation in a low temperature region, and the admittance Y is calculated to use the temperature estimation in a high temperature region, taking the temperature characteristics of the impedance Z and the admittance Y into consideration.

However, the conventional method for estimating an element temperature as described in Patent Literature 1 is susceptible to further improvement for estimating an element temperature of a sensor with high accuracy.

Patent Literature 1: JP-2000-65781-A

SUMMARY

It is an object of the present disclosure to provide an applied voltage control device which is used for a sensor and is capable of estimating an element temperature with high accuracy.

According to an aspect of the present disclosure, an applied voltage control device for a sensor, in which a direct current corresponding to an oxygen amount flows when a DC voltage is applied to the sensor, and an alternating current corresponding to a sensor impedance flows when an AC voltage is applied to the sensor, includes: a filtering unit that sets a cut-off frequency of the AC voltage applied to the sensor variable.

The above applied voltage control device enables the cut-off frequency of the AC voltage to be appropriately set in response to, for example, changes in the element temperature of the sensor. Thus, it is possible to improve the accuracy of detecting the sensor impedance of the sensor and estimate the element temperature of the sensor derived from the sensor impedance with high accuracy.

Thus, the above applied voltage control device makes it possible to provide an applied voltage control device which is used for a sensor and is capable of estimating an element temperature with high accuracy.

BRIEF DESCRIPTION OF THE DRAWINGS

The above and other objects, features and advantages of the present disclosure will become more apparent from the following detailed description made with reference to the accompanying drawings. In the drawings:

FIGS. 5A to 5F are time charts for describing an example of the behavior of the cut-off frequency switching processing in the first embodiment;

FIGS. 7A to 7F are time charts for describing an example of the behavior of the cut-off frequency switching processing in the second embodiment;

FIGS. 8A to 8F are time charts for describing an example of the behavior of cut-off frequency switching processing in a modification of the second embodiment;

FIGS. 10A to 10F are time charts for describing an example of the behavior of the cut-off frequency switching processing in the third embodiment;

FIGS. 12A to 12F are time charts for describing an example of the behavior of the cut-off frequency switching processing in the fourth embodiment;

FIGS. 14A to 14F are time charts for describing an example of the behavior of the cut-off frequency switching processing in the fifth embodiment.

DETAILED DESCRIPTION

Hereinbelow, embodiments of the present disclosure will be described with reference to the accompanying drawings.

To facilitate understanding of the description, identical elements are denoted by identical reference signs throughout the drawings as far as possible, and overlapping description is omitted.

(First Embodiment)

Figure 1:
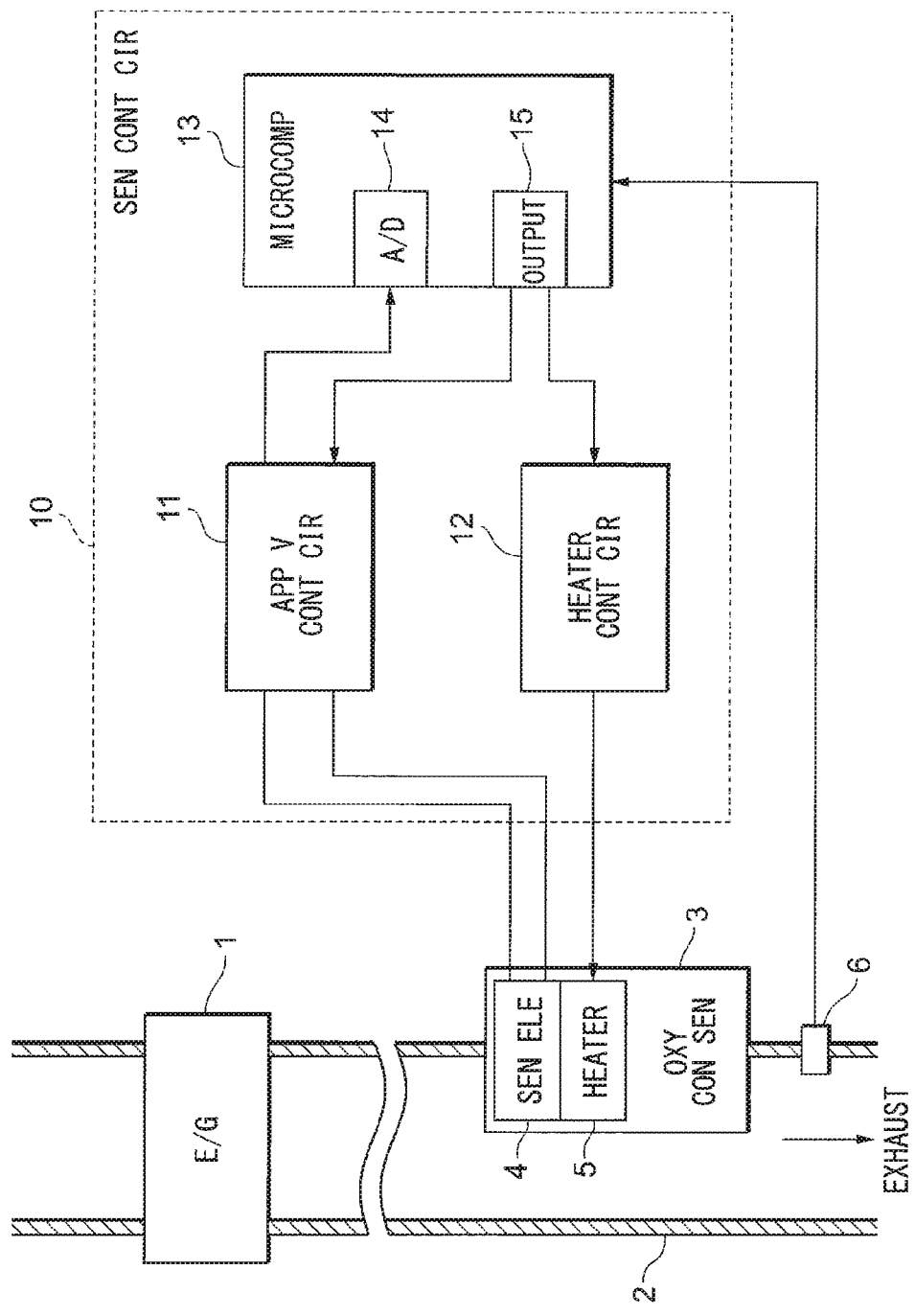
FIG. 1 is a block diagram illustrating a schematic configuration of a senor control device for an oxygen content sensor, the sensor control device including an applied voltage control circuit (applied voltage control device) according to a first embodiment of the present disclosure.

A first embodiment will be described with reference to FIGS. 1 to 5F. As illustrated in FIG. 1, in the present embodiment, an oxygen content sensor 3 is described as an example of a sensor that allows a direct current corresponding to an oxygen amount to flow therethrough by the application of a direct-current (DC) voltage, and an applied voltage control circuit 11 is described as an example of an applied voltage control device that controls a voltage applied to the oxygen content sensor 3. As illustrated in FIG. 1, the applied voltage control circuit 11 as the applied voltage control device according to an embodiment of the present disclosure is incorporated as a part of a sensor control device 10 which controls the operation of the oxygen content sensor 3.

The oxygen content sensor 3 is placed in an exhaust pipe 2 of an engine 1 to detect the oxygen content in an exhaust gas (gas to be detected). The oxygen content sensor 3 is a limiting current sensor which includes a sensor element 4 having a characteristic of allowing a direct current Idc (hereinbelow, also referred to as "sensor output current") corresponding to the oxygen content to flow therethrough by the application of a direct-current (DC) voltage Vdc and generates a limiting current that is substantially proportional to the oxygen content in an exhaust gas. That is, the oxygen content sensor 3 changes the direct current Idc to be output according to the oxygen content in an exhaust gas flowing through the exhaust pipe 2. The direct current Idc output from the oxygen content sensor 3 increases as the oxygen content in the exhaust gas increases. On the other hand, the direct current Idc output from the oxygen content sensor 3 decreases as the oxygen content in the exhaust gas decreases.

The sensor element 4 of the oxygen content sensor 3 also has a characteristic of allowing an alternating current Iac (hereinbelow, also referred to as "sensor output current") to flow therethrough by the application of an alternating-current (AC) voltage Vac.

The sensor element 4 of the oxygen content sensor 3 includes, for example, a solid electrolyte layer made of partially stabilized zirconia, and becomes an active state at a temperature within a predetermined active temperature range (700° C. or more, for example) so as to generate the sensor output current according to the oxygen content. A heater 5 is built in the oxygen content sensor 3 to maintain the temperature of the sensor element 4 within the active temperature range. The generation of heat by the heater 5 enables the temperature of the sensor element 4 to be increased.

An exhaust gas temperature sensor 6 is set in the exhaust pipe 2 of the engine 1 to detect the temperature of an exhaust gas (exhaust gas temperature Te) inside the exhaust pipe 2. The exhaust gas temperature sensor 6 outputs information about the detected exhaust gas temperature Te to a microcomputer 13 of the sensor control device 10.

The sensor control device 10 is provided with the applied voltage control circuit 11, a heater control circuit 12, and the microcomputer 13.

Figure 2:
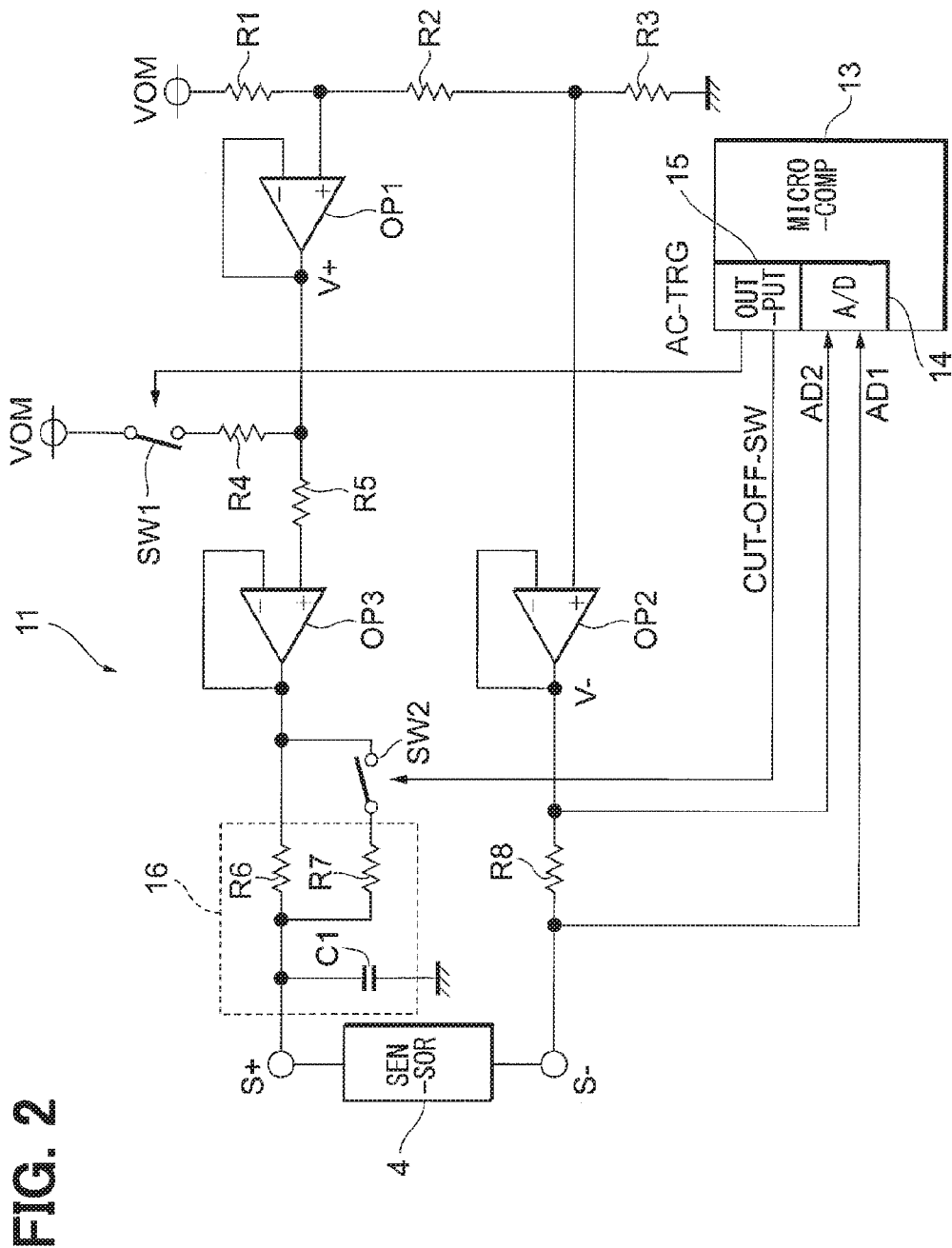
FIG. 2 is a circuit diagram illustrating an example of the configuration of the applied voltage control circuit in FIG. 1.

As illustrated in FIGS. 1 and 2, the applied voltage control circuit 11 is electrically connected to the sensor element 4 of the oxygen content sensor 3. The applied voltage control circuit 11 controls a voltage (the AC voltage Vac, the DC voltage Vdc) applied to the sensor element 4 and acquires a voltage value corresponding to the sensor output current (the alternating current Iac, the direct current Idc) output from the sensor element 4. The applied voltage control circuit 11 is also electrically connected to the microcomputer 13. The applied voltage control circuit 11 controls the applied voltage Vac, Vdc in accordance with a command signal (AC-TRG and CUT-OFF-SW in FIG. 2) from the microcomputer 13 and outputs a voltage value (AD1, AD2 in FIG. 2) corresponding to the sensor output current Iac, Idc acquired from the sensor element 4 to the microcomputer 13.

The heater control circuit 12 is electrically connected to the heater 5 of the oxygen content sensor 3 and the microcomputer 13, and controls a heat generation amount of the heater 5 in accordance with a command signal from the microcomputer 13. The heater control circuit 12 can control the heat generation amount of the heater 5, for example, by controlling a duty factor (duty) of the heater 5.

The microcomputer 13 controls the operation of the oxygen content sensor 3 through the applied voltage control circuit 11 and the heater control circuit 12. The microcomputer 13 acquires a voltage value corresponding to the sensor output current Iac, Idc from the applied voltage control circuit 11 through an A/D converter 14 (referred to as "A/D" in FIGS. 1 and 2). The microcomputer 13 outputs command signals to the applied voltage control circuit 11 and the heater control circuit 12 through a D/A converter 15 (referred to as "OUTPUT" in FIGS. 1 and 2).

The microcomputer 13 controls the applied voltage control circuit 11 to apply a desired DC voltage Vdc to the sensor element 4 of the oxygen content sensor 3 and acquires a voltage value corresponding to a direct current Idc that is output from the oxygen content sensor 3 in response to the application of the DC voltage Vdc from the applied voltage control circuit 11. The microcomputer 13 can calculate the direct current Idc from the voltage value acquired from the applied voltage control circuit 11 and calculate the oxygen content of the exhaust gas on the basis of the calculated direct current Idc.

The microcomputer 13 controls the applied voltage control circuit 11 to apply a desired AC voltage Vac to the sensor element 4 of the oxygen content sensor 3 and acquires a voltage value corresponding to an alternating current Iac that is output in response to the application of the AC voltage Vac from the applied voltage control circuit 11. The microcomputer 13 calculates the alternating current Iac from the voltage value acquired from the applied voltage control circuit 11 and calculates a sensor impedance Zac of the oxygen content sensor 3 on the basis of the calculated sensor output current Iac and the AC voltage Vac. The sensor impedance Zac can be derived by dividing the AC voltage Vac applied to the oxygen content sensor 3 by the alternating current Iac output from the oxygen content sensor 3 in response to the application of the AC voltage Vac (Zac=Vac/Iac). In other words, the alternating current Iac corresponding to the sensor impedance Zac flows through the oxygen content sensor 3 by applying the AC voltage Vac to the oxygen content sensor 3.

The large-small relation in the sensor impedance Zac corresponds to the high-low relation in an element temperature of the oxygen content sensor 3. When the sensor impedance is relatively large, the element temperature is relatively high. When the sensor impedance is relatively small, the element temperature is relatively low (the large-small relation in the impedance may be the inverse of the high-low relation in the element temperature depending on the circuit configuration). That is, the microcomputer 13 can indirectly acquire the element temperature of the oxygen content sensor 3 on the basis of the sensor impedance Zac.

Further, the microcomputer 13 can acquire "element temperature related information" related to the temperature of the sensor element 4 (element temperature) of the oxygen content sensor 3 from, for example, the applied voltage control circuit 11, and estimate the element temperature or indirectly acquire the element temperature on the basis of the element temperature related information. In the present embodiment, the sensor impedance Zac of the oxygen content sensor 3 is used as the element temperature related information.

The microcomputer 13 feedback-controls the heater control circuit 12 on the basis of the element temperature estimated in this manner so that an actual temperature of the sensor element 4 of the oxygen content sensor 3 becomes a desired set temperature. The microcomputer 13 can appropriately set the set temperature of the sensor element 4 within the active temperature region according to, for example, an operating state of the engine 1 (for example, so that the fuel consumption falls within a high efficiency region).

In the present embodiment, due to constraints in the size and installation space of the oxygen content sensor 3 and cost, an actual temperature of the sensor element 4 is not directly measured by, for example, a temperature sensor, but the microcomputer 13 estimates the element temperature on the basis of the sensor impedance Zac which has a relationship with the element temperature. Thus, a low accuracy of the estimation of the temperature of the sensor element 4 may cause the following problem. When the set temperature is set around the boundary of the active temperature region, an actual element temperature may fall out of the active temperature region and the oxygen content sensor 3 may not function even when the element temperature is controlled by the feedback control. In order to avoid such a situation, it is desired to estimate the element temperature with high accuracy at least in a range including the active temperature region.

Figure 3:
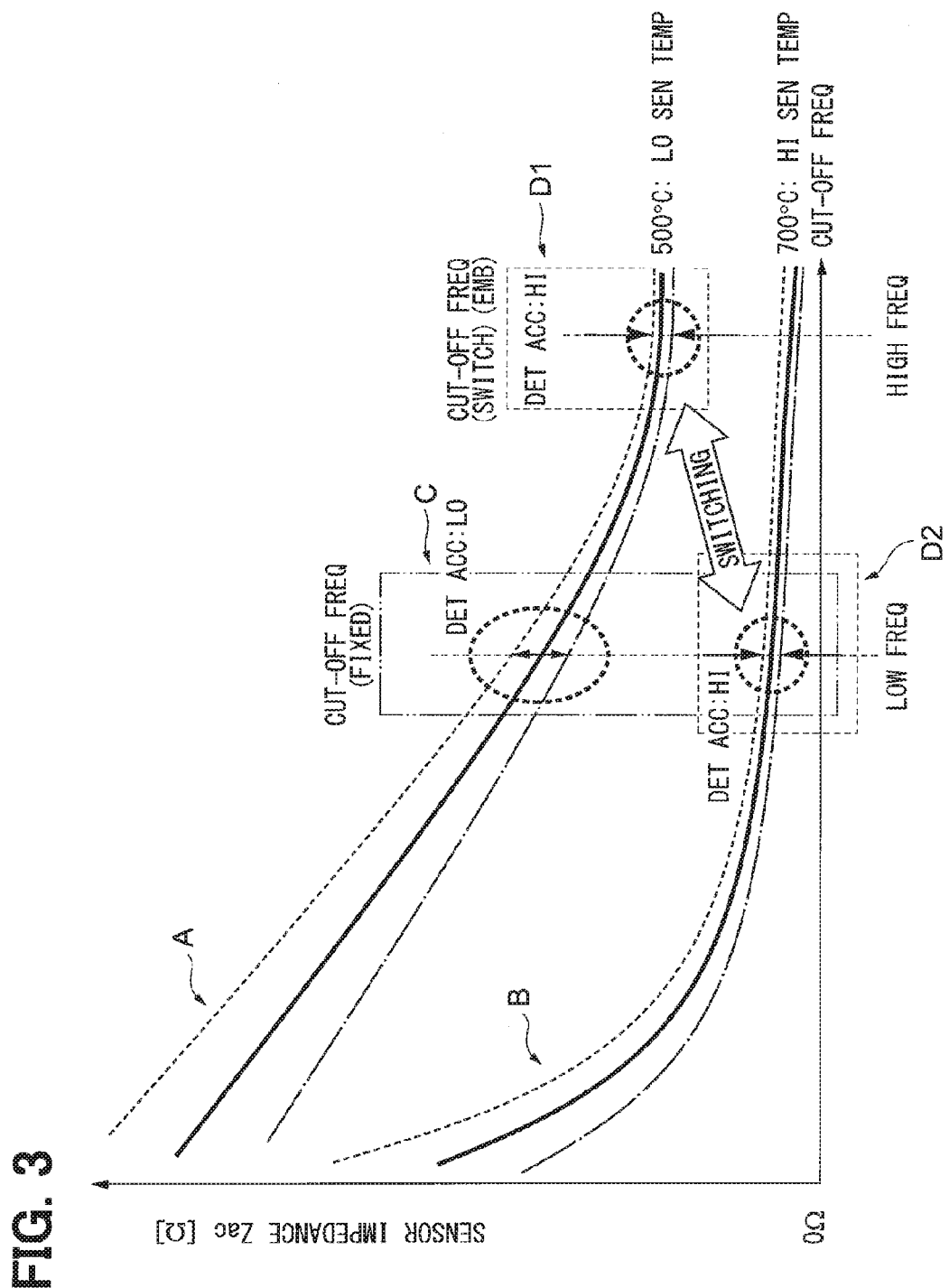
FIG. 3 is a diagram illustrating the relationship between a sensor impedance-cut-off frequency characteristic and a sensor element temperature.

In the sensor control device 10 illustrated in FIG. 1, the AC voltage Vac generated in the applied voltage control circuit 11 is generally subjected to filtering for removing a high frequency component with a predetermined cut-off frequency and thereafter applied to the sensor element 4. The relationship between the cut-off frequency, and the sensor impedance Zac and the element temperature will be described with reference to FIG. 3. FIG. 3 illustrates graphs A and B of a characteristic of the relationship between the cut-off frequency and the sensor impedance. In FIG. 3, the vertical axis represents the sensor impedance Zac, and the horizontal axis represents the cut-off frequency. The graph A shows a sensor impedance-cut-off frequency characteristic when the element temperature is in a low temperature state of 500° C. The graph B shows a sensor impedance-cut-off frequency characteristic when the element temperature is in a high temperature state of 700° C. In each of the graphs A, B, a representative value of a sensor individual characteristic is indicated by a sold line, a maximum value thereof is indicated by a dotted line, and a minimum value thereof is indicated by a dot-dash line.

As illustrated in the graph A or the graph B of FIG. 3, the sensor impedance Zac decreases as the cut-off frequency becomes higher in the same element temperature. The sensor output current Iac increases as the sensor impedance Zac decreases, which may increase the size of a circuit and increase cost. Thus, it is preferred to set the cut-off frequency at the low frequency side so that the sensor impedance Zac can be detected in a region in which the sensor impedance Zac is large.

As illustrated in the graph A and the graph B of FIG. 3, the sensor impedance-cut-off frequency characteristic makes a transition to a positive direction and the sensor impedance Zac corresponding to the cut-off frequency increases as the element temperature decreases in different element temperatures. Further, there is a tendency that variation in the sensor impedance Zac (the width between the maximum value and the minimum value) increases as the cut-off frequency becomes lower. This tendency becomes more conspicuous as the element temperature decreases. That is, the graph A representing the characteristic in a low temperature region has a larger variation in the sensor impedance Zac than the graph B representing the characteristic in a high temperature region. Further, in the graph A, the tendency of increasing the variation at the low frequency side is started at a relatively high frequency side. The large variation in the sensor impedance Zac may deteriorate the detection accuracy of the sensor. Thus, the cut-off frequency is preferably set in a region having a large sensor impedance Zac and having a small variation in the sensor impedance Zac in the sensor impedance-cut-off frequency characteristic.

In a conventional control method for the oxygen content sensor 3, a single cut-off frequency is fixed to be used. In this case, the cut-off frequency is set so as to have high accuracy of detection of the sensor impedance Zac at the active temperature (700° C., for example) of the oxygen content sensor 3. That is, as illustrated as a region C in FIG. 3, the cut-off frequency is set on the basis of the characteristic of the sensor high temperature region corresponding to the sensor active temperature (the graph B of FIG. 3) so that the sensor impedance Zac is relatively large and the variation in the sensor impedance Zac is small in this characteristic. When the cut-off frequency is set so as to have high accuracy of the detection of the sensor impedance Zac during such a high temperature of the sensor, there is a tendency that variation in the sensor individual characteristic increases and the accuracy of the detection of the sensor impedance Zac becomes lower as the element temperature decreases as illustrated in the graph A.

On the other hand, in the present embodiment, the cut-off frequency is switched between when the element temperature of the oxygen content sensor 3 is in a high temperature state and when the element temperature of the oxygen content sensor 3 is in a low temperature state as illustrated as regions D1 and D2 in FIG. 3. When the element temperature is in a high temperature state, similarly to the conventional method, the cut-off frequency is set on the basis of the characteristic of the sensor high temperature region (the graph B of FIG. 3) so that the sensor impedance Zac is large and the variation in the sensor impedance Zac is small in this characteristic as illustrated as the region D2 in FIG. 3. Accordingly, when the element temperature is in a high temperature state, the sensor impedance Zac can be detected in a region in which the sensor impedance Zac is large. On the other hand, when the element temperature is in a low temperature state, the cut-off frequency is set to be relatively higher than that in a high temperature state (region D2) as illustrated as the region D1 in FIG. 3. Thus, even in the characteristic of the sensor low temperature region (the graph A of FIG. 3) with the sensor temperature in a low temperature state, the cut-off frequency is set so as to reduce the variation in the sensor impedance Zac. Accordingly, even when the element temperature is in a low temperature state, the sensor impedance Zac can be detected in a region in which the variation in the sensor impedance Zac is small. Thus, it is possible to improve the accuracy of the detection of the sensor impedance Zac regardless of the element temperature of the oxygen content sensor 3 and thereby estimate the element temperature with high accuracy.

The function of switching the cut-off frequency of the AC voltage Vac applied to the oxygen content sensor 3 is achieved by the microcomputer 13 and the applied voltage control circuit 11 in the present embodiment.

The microcomputer 13 determines the necessity of changing the cut-off frequency on the basis of the element temperature related information. In the first embodiment, the sensor impedance Zac is used as the element temperature related information as described above. Further, the large-small relation in the sensor impedance Zac corresponds to the high-low relation in the element temperature of the oxygen content sensor 3. Thus, when the sensor impedance Zac is relatively high, the microcomputer 13 determines that the element temperature is in a relatively low state and sets the cut-off frequency to be relatively high. On the other hand, when the sensor impedance Zac is relatively low, the microcomputer 13 determines that the element temperature is in a relatively high state and sets the cut-off frequency to be relatively low. Thus, the microcomputer 13 determines to change the cut-off frequency from a high frequency one to a low frequency one when the sensor impedance Zac makes a transition from a state of a predetermined threshold or more (low temperature region) to a state of the threshold or less (high temperature region) through the threshold. Similarly, the microcomputer 13 determines to change the cut-off frequency from the low frequency one to the high frequency one when the sensor impedance Zac makes a transition from a state of the predetermined threshold or less (high temperature region) to a state of the threshold or more (low temperature region) through the threshold. Upon determining the change of the cut-off frequency, the microcomputer 13 outputs a command signal (CUT-OFF-SW in FIG. 2) corresponding to the change to the applied voltage control circuit 11, and the applied voltage control circuit 11 switches the cut-off frequency of the AC voltage Vac in response to the reception of the command signal.

The microcomputer 13 is configured as a computer system provided with a CPU, a ROM, a RAM, and an input/output interface (the A/D converter 14 and the D/A converter 15). The microcomputer 13 is implemented as, for example, a part of an electronic control unit (ECU) of a vehicle on which the control device 10 is mounted.

A specific circuit configuration of the applied voltage control circuit 11 may be, for example, as illustrated in FIG. 2. The applied voltage control circuit 11 is provided with three operational amplifiers OP1, OP2, OP3, eight resistors R1 to R8, a capacitor C1, an AC voltage generation switch SW1, and a cut-off frequency change switch SW2. The resistor R1, the resistor R2, and the resistor R3 are connected in series. The resistor R1 is connected to a constant power source VOM. The resistor R3 is grounded. A positive side input terminal of the operational amplifier OP1 is connected to an intermediate point between the resistor R1 and the resistor R2. A positive side input terminal of the operational amplifier OP2 is connected to an intermediate point between the resistor R2 and the resistor R3.

An output terminal of the operational amplifier OP1 is connected to a negative side input terminal of the operational amplifier OP1 and a positive side input terminal of the operational amplifier OP3. The resistor R5 is disposed between the output terminal of the operational amplifier OP1 and the positive side input terminal of the operational amplifier OP3. A constant power source VOM is connected to an intermediate point between the resistor R5 and the output terminal of the operational amplifier OP1 through the AC voltage generation switch SW1 and the resistor R4. An output terminal of the operational amplifier OP3 is connected to a negative side input terminal of the operational amplifier OP3, and further connected to the resistor R6 and the resistor R7 in parallel. The resistor R6 is connected to a positive side terminal S+ of the sensor element 4. The capacitor C1 is connected to an intermediate point between the resistor R6 and the positive side terminal S+. The capacitor C1 is grounded. The cut-off frequency change switch SW2 is disposed between the resistor R7 and the operational amplifier OP3.

The AC voltage generation switch SW1 is switched between an ON state and an OFF state in accordance with a command signal AC-TRG output from the D/A converter (output) of the microcomputer 13. In the applied voltage control circuit 11, the AC voltage generation switch SW1 is alternately switched between an ON state and an OFF state to generate an AC voltage Vac. In the applied voltage control circuit 11, a part that includes the resistor R6, the resistor R7, and the capacitor C1 serves as a filter circuit 16 (filtering unit) for low-pass filtering the generated AC voltage. That is, the AC voltage Vac generated in the applied voltage control circuit 11 is subjected to the low-pass filtering in the filter circuit 16 and thereafter applied to the sensor element 4 of the oxygen content sensor 3. The positive side terminal S+ and a negative side terminal S− of the oxygen content sensor 3 may be reversed depending on the circuit configuration of the applied voltage control circuit 11. In other words, the position of the positive side terminal S+ and the position of the negative side terminal S− of the oxygen content sensor 3 which is disposed in parallel to the capacitor C1 may be reversed depending on the circuit configuration of the applied voltage control circuit 11.

The cut-off frequency change switch SW2 is switched between an ON state and an OFF state in accordance with the command signal CUT-OFF-SW output from the D/A converter (output) of the microcomputer 13. When the cut-off frequency change switch SW2 is in an ON state, the resistor R7 becomes an energized state. On the other hand, when the cut-off frequency change switch SW2 is in an OFF state, the resistor R7 becomes a non-energized state. The filter circuit 16 enables a filter time constant (cut-off frequency) in the low-pass filtering to be variable by the switching of the cut-off frequency change switch SW2 between an ON state and an OFF state.

An output terminal of the operational amplifier OP2 is connected to a negative side input terminal of the operational amplifier OP2 and the resistor R8. The resistor R8 is connected to the negative side terminal S− of the sensor element 4. A signal line is connected to an intermediate point between the resistor R8 and the negative side terminal S− of the sensor element 4 and a signal line is connected to an intermediate point between the resistor R8 and the output terminal of the operational amplifier OP2 so that voltage values AD1, AD2 in these intermediate points can be output to the A/D converter 14 of the microcomputer 13. The microcomputer 13 can calculate the sensor output currents Iac, Idc on the basis of these voltage values AD1, AD2.

In the applied voltage control circuit 11, the AC voltage generation switch SW1 is maintained in an OFF state (or an ON state) to generate the DC voltage Vdc.

Figure 4:
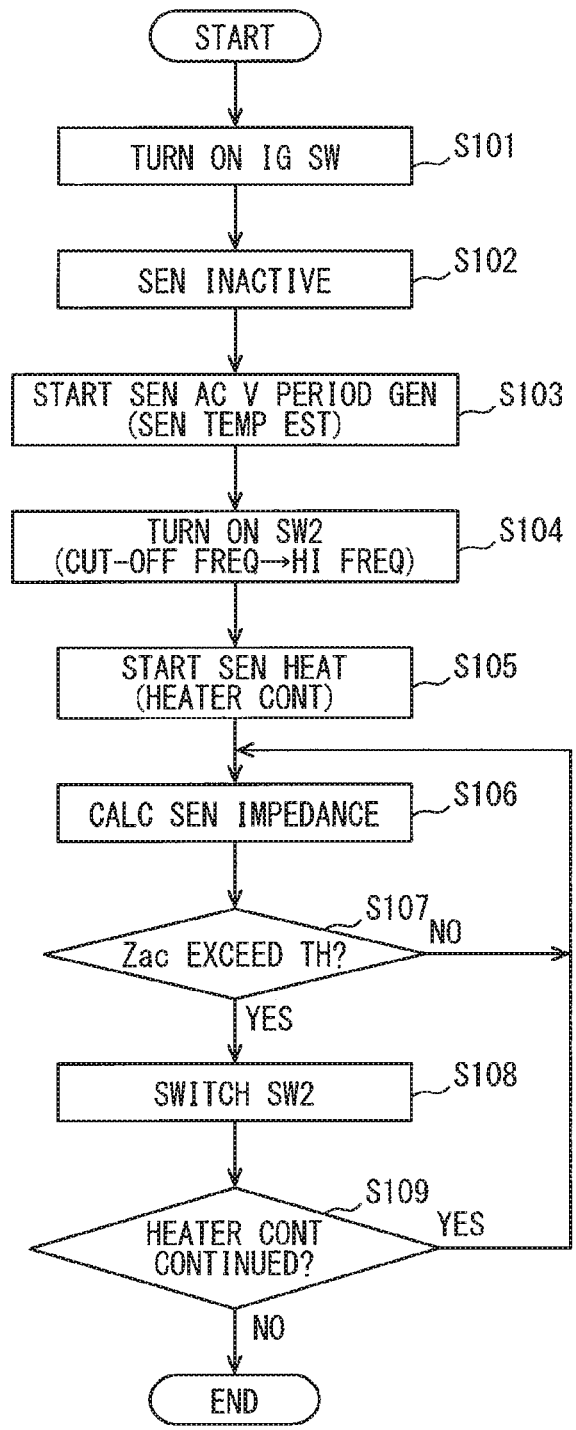
FIG. 4 is a flow chart illustrating cut-off frequency switching processing in the first embodiment.

Next, processing of switching the cut-off frequency of the applied voltage control circuit 11 in the first embodiment will be described with reference to a flow chart of FIG. 4 and time charts of FIGS. 5A to 5F. A series of processes in the time chart of FIG. 4 is performed by the sensor control device 10 when the engine 1 is in an operating state. The time charts of FIGS. 5A to 5F illustrates (a) engine state, (b) sensor temperature (an actual element temperature of the oxygen content sensor 3), (c) CUT-OFF-SW (a control signal for the cut-off frequency change switch SW2 in the applied voltage control circuit 11), (d) cut-off frequency, (e) AC voltage (AC voltage Vac) applied waveform, and (f) change in sensor impedance Zac with time during the cut-off frequency switching processing. Hereinbelow, description will be made following the flow chart of FIG. 4 and referring to the time charts of FIGS. 5A to 5F.

After an ignition switch of the vehicle is turned ON in step S101, the generation of a period of a sensor AC voltage (AC voltage Vac) is started in step S103 in a sensor inactive state (that is, the element temperature of the oxygen content sensor 3 is low and the sensor is thus inactive) of step S102. That is, the applied voltage control circuit 11 generates the AC voltage Vac in accordance with the command signal AC-TRG from the microcomputer 13 and starts the application of the AC voltage Vac to the sensor element 4 of the oxygen content sensor 3. Specifically, the microcomputer 13 appropriately switches the command signal AC-TRG for the AC voltage generation switch SW1 of the applied voltage control circuit 11 to switch the AC voltage generation switch SW1 between an ON state and an OFF state. Accordingly, the AC voltage Vac is generated in the applied voltage control circuit 11. In addition to this, the microcomputer 13 starts temperature estimation using the sensor impedance Zac. After completion of the process of step S103, the processing proceeds to step S104.

In step S104, the cut-off frequency change switch SW2 is switched to an ON state to change the cut-off frequency of the applied voltage control circuit 11 to the high frequency side. After completion of the process of step S104, the processing proceeds to step S105.

In the time charts of FIGS. 5A to 5F, as illustrated in FIG. 5B, the sensor temperature is low and the oxygen content sensor 3 is in an inactive state in a section before time t0. Then, as illustrated in FIG. 5E, the generation of the AC voltage Vac in step S103 is started so that output of a periodic waveform of the AC voltage Vac is started at the time t0. Further, at the time t0, the switching of the cut-off frequency change switch SW2 to an ON state in step S104 is performed as illustrated in FIG. 5C to change the cut-off frequency of the applied voltage control circuit 11 to the high frequency side as illustrated in FIG. 5D.

In step S105, sensor heating is started. The microcomputer 13 starts feedback control (heater control) by the heater control circuit 12 on the basis of the element temperature of the oxygen content sensor 3 the estimation of which is started in step S103 so that the element temperature becomes a predetermined set temperature (which is determined within the active temperature region on the basis of, for example, an operating state of the engine 1). During the heater control, the heater control circuit 12, for example, appropriately controls the duty factor (duty) of the heater 5 to control the heat generation amount of the heater 5. After completion of step S105, the processing proceeds to step S106.

In the time charts of FIGS. 5A to 5F, the sensor heating (heater control) is started at the time t0 as illustrated in FIG. 5B. In a section after the time to, the sensor temperature increases to 700° C. which is set as the set temperature (referred to as "CONTROL TARGET TEMPERATURE" in FIGS. 5A to 5F).

In step S106, the sensor impedance Zac is calculated. As illustrated in FIG. 2, the microcomputer 13 acquires the voltage values AD1, AD2 on both ends of the resistor R8 in the applied voltage control circuit 11 and calculates a value of current flowing through the resistor R8, that is, the sensor output current Iac flowing through the applied voltage control circuit 11 on the basis of these voltage values AD1, AD2. The microcomputer 13 also acquires the AC voltage Vac applied from the applied voltage control circuit 11 to the oxygen content sensor 3 and calculates the sensor impedance Zac by dividing the AC voltage Vac by the sensor output current Iac (Zac=Vac/Iac). After completion of the process of step S106, the processing proceeds to step S107.

In step S107, it is determined whether the sensor impedance Zac has exceeded a threshold. As the threshold, a threshold employed when the sensor temperature makes a transition from the low temperature region to the high temperature region (TH1 in FIGS. 5A to 5F, for example) and a threshold employed when the temperature makes a transition from the high temperature region to the low temperature region (TH2 in FIGS. 5A to 5F, for example) may be individually set as illustrated in FIG. 5F, or a threshold that is common in transitions in both directions may be set. When the result of the determination of step S107 shows that the sensor impedance Zac has not exceeded the threshold (No in step S107), the processing returns to step S106. When the sensor impedance Zac has exceeded the threshold (Yes in step S107), the processing proceeds to step S108.

Since the sensor impedance Zac has exceeded the threshold in step S107, the cut-off frequency change switch SW2 is switched in step S108. Specifically, the cut-off frequency change switch SW2 is switched to an OFF state when in an ON state or switched to an ON state when in an OFF state. After completion of the process of step S108, the processing proceeds to step S109.

In step S109, it is determined whether the heater control has been continued. When the result of the determination of step S109 shows that the heater control has been continued (Yes in step S109), the processing returns to step S106, and the processes of steps S106 to S108 are repeated. On the other hand, when the heater control has been finished (No in step S109), the control flow is finished.

In the time charts of FIGS. 5A to 5F, the sensor impedance Zac continuously decreases with increase in the sensor temperature in a section from the time t0 to time t1 as illustrated in FIG. 5F. In this section, the sensor impedance Zac has not exceeded the threshold TH1 employed when the sensor temperature makes a transition from the low temperature region to the high temperature region. Thus, steps S106, S107 are repeated. At this time, in the sensor impedance-cut-off frequency characteristic of FIG. 3, the cut-off frequency is set to the one in the region D1 at the high frequency side.

When the sensor impedance Zac exceeds the threshold TH1 at the time t1, the cut-off frequency change switch SW2 is switched to an OFF state as illustrated in FIG. 5C to change the cut-off frequency to the low frequency one. At this time, in the sensor impedance-cut-off frequency characteristic of FIG. 3, the cut-off frequency makes a transition to the region D2 at the low frequency side. Accordingly, the sensor impedance-cut-off frequency characteristic is switched from the characteristic in the low temperature region (graph A) to the characteristic in the high temperature region (graph B). With the switching of the cut-off frequency, the sensor impedance Zac increases in a step-like manner at the time t1 as illustrated in FIG. 5F. Further, at the time t1, the sensor temperature has reached the control target temperature as illustrated in FIG. 5B and sensor warming-up has been completed. Alternatively, there may be control of previously switching the cut-off frequency when the sensor temperature reaches a high temperature before the completion of the warming-up. In this case, for example, the threshold TH1 of the sensor impedance Zac may be set to be smaller than that in the example of FIGS. 5A to 5F so that the sensor impedance Zac exceeds the threshold TH1 before the completion of the sensor warming-up.

In a section from the time t1 to time t2, as illustrated in FIG. 5B, a state of the sensor temperature exceeding the control target temperature is maintained, and the sensor temperature starts decreasing when the engine state is switched from a normal state to a stopped state at the time t2. In a section from the time t2 to time t3, the sensor impedance Zac continuously increases with decrease in the sensor temperature as illustrated in FIG. 5F. In this section, the sensor impedance Zac has not exceeded the threshold TH2 employed when the sensor temperature makes a transition from the high temperature region to the low temperature region. Thus, steps S106, S107 are repeated. At this time, in the sensor impedance-cut-off frequency characteristic of FIG. 3, the cut-off frequency remains in the region D2 at the low frequency side.

When the sensor impedance Zac exceeds the threshold TH2 at the time t3, the cut-off frequency change switch SW2 is switched to an ON state as illustrated in FIG. 5C to again change the cut-off frequency to the high frequency one. At this time, in the sensor impedance-cut-off frequency characteristic of FIG. 3, the cut-off frequency again makes a transition to the region D1 at the high frequency side. With the switching of the cut-off frequency, the sensor impedance Zac decreases in a step-like manner at the time t3 as illustrated in FIG. 5F. After the time t3, the sensor temperature continuously decreases as illustrated in FIG. 5B and reaches an initial value at time t4. With the decrease in the sensor temperature, the sensor impedance Zac increases as illustrated in FIG. 5F.

An effect of the applied voltage control circuit 11 (the applied voltage control device) according to the first embodiment will be described. As described above with reference to FIG. 3, in the configuration using a single cut-off frequency, the cut-off frequency is set so that the accuracy of the detection of the sensor impedance Zac is high (that is, the sensor impedance Zac is relatively large and the variation in the sensor impedance Zac is small) near the active temperature of the oxygen content sensor 3 (high temperature region). Thus, there is a tendency that the variation in the sensor individual characteristic increases and the accuracy of the detection of the sensor impedance Zac is reduced as the element temperature comes close to the low temperature side. As a result, there may be a variation in the accuracy of detecting the sensor impedance Zac of the oxygen content sensor 3. On the other hand, in the applied voltage control circuit 11 of the present embodiment, the cut-off frequency of the AC voltage Vac applied to the oxygen content sensor 3 is variable. Thus, it is possible to set an appropriate cut-off frequency in response to, for example, changes in the element temperature of the oxygen content sensor 3. Accordingly, the accuracy of detecting the sensor impedance Zac of the oxygen content sensor 3 can be improved. As a result, the element temperature of the oxygen content sensor 3 derived from the sensor impedance Zac can be estimated with high accuracy. Further, the improvement in the accuracy of the element temperature estimation enables the sensor control device 10 to accurately perform temperature control for the oxygen content sensor 3. As a result, the detection accuracy of the oxygen content sensor 3 can be improved.

As described above with reference to FIG. 3, the sensor impedance-cut-off frequency characteristic varies in response to changes in the element temperature. Thus, it is conceivable that the variation in the accuracy of the detection of the sensor impedance Zac that is generated when a single cut-off frequency is used is highly affected by changes in the element temperature. On the other hand, in the applied voltage control circuit 11 of the first embodiment, the cut-off frequency is variable in accordance with a command signal from the microcomputer 13 based on the element temperature related information related to the element temperature of the oxygen content sensor 3. Specifically, the cut-off frequency is set to be relatively high when the element temperature is relatively low and set to be relatively low when the element temperature is relatively high on the basis of the element temperature related information. This enables an appropriate cut-off frequency to be set according to the element temperature which highly affects the variation in the accuracy of the detection of the sensor impedance Zac. Thus, it is possible to facilitate the improvement in the accuracy of detecting the sensor impedance Zac of the oxygen content sensor 3 and further improve the accuracy of estimating the element temperature of the oxygen content sensor 3.

In the first embodiment, the sensor impedance Zac is used as the element temperature related information. When the sensor impedance Zac is relatively high, the element temperature is determined to be relatively low, and the cut-off frequency is set to be relatively high. On the other hand, when the sensor impedance Zac is relatively low, the element temperature is determined to be relatively high, and the cut-off frequency is set to be relatively low. The large-small relation in the sensor impedance Zac corresponds to the high-low relation in the element temperature of the oxygen content sensor 3 and is information that appropriately reflects changes in the element temperature. Thus, it is possible to accurately acquire changes in the element temperature and further improve the accuracy of estimating the element temperature of the oxygen content sensor 3.

(Second Embodiment)

Figure 6:
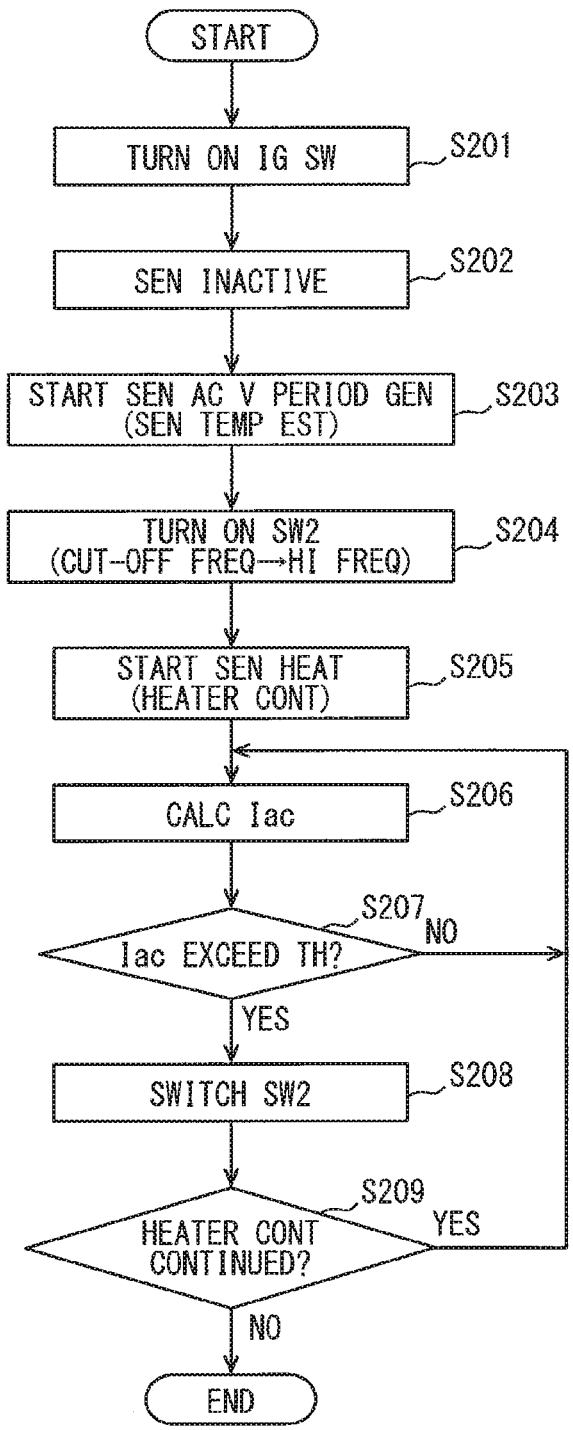
FIG. 6 is a flow chart illustrating cut-off frequency switching processing in a second embodiment.

Next, a second embodiment will be described with reference to FIGS. 6 and 7A to 7F. As illustrated in FIG. 6, the second embodiment differs from the first embodiment in that a sensor output current Iac (alternating current Iac) is used as the element temperature related information related to the element temperature of the oxygen content sensor 3 and the cut-off frequency is variable on the basis of the sensor output current Iac.

As illustrated in FIGS. 7B and 7F, the large-small relation in the sensor output current Iac also corresponds to the high-low relation in the element temperature of the oxygen content sensor 3 similarly to the sensor impedance Zac. The sensor output current Iac which is used in determination of switching of the cut-off frequency in the present embodiment indicates an index value corresponding to the size of an alternating current output from the oxygen content sensor 3 such as an effective value or a half-wave average value of the alternating current.

Processing of switching the cut-off frequency of the applied voltage control circuit 11 in the second embodiment will be described with reference to a flow chart of FIG. 6 and time charts of FIGS. 7A to 7F. A series of processes in the time chart of FIG. 6 is performed by the sensor control device 10 when the engine 1 is in an operating state. The time charts of FIGS. 7A to 7F illustrates (a) engine state, (b)

sensor temperature (an actual element temperature of the oxygen content sensor 3), (c) CUT-OFF-SW (a control signal for the cut-off frequency change switch SW2 in the applied voltage control circuit 11), (d) cut-off frequency, (e) AC voltage (AC voltage Vac) applied waveform, and (f) change in sensor output current Iac (AC current Iac) with time during the cut-off frequency switching processing. Hereinbelow, description will be made following the flow chart of FIG. 6 and referring to the time charts of FIGS. 7A to 7F. Since processes of steps S201 to S205 are respectively similar to the processes of steps S101 to S105 of FIG. 4, description thereof will be omitted.

In step S206, the sensor output current Iac is calculated. As illustrated in FIG. 2, the microcomputer 13 acquires voltage values AD1, AD2 on both ends of the resistor R8 in the applied voltage control circuit 11, and calculates a value of current flowing through the resistor R8, that is, the sensor output current Iac flowing through the applied voltage control circuit 11 on the basis of these voltage values AD1, AD2. After completion of the process of step S206, the processing proceeds to step S207.

In step S207, it is determined whether the sensor output current Iac has exceeded a threshold THIac. When the result of the determination of step S207 shows that the sensor output current Iac has not exceeded the threshold THIac (No in step S207), the processing returns to step S206. When the sensor output current Iac has exceeded the threshold (Yes in step S207), the processing proceeds to step S208.

Since the sensor output current Iac has exceeded the threshold in step S207, the cut-off frequency change switch SW2 is switched in step S208. Specifically, the cut-off frequency change switch SW2 is switched to an OFF state when in an ON state or switched to an ON state when in an OFF state. After completion of the process of step S208, the processing proceeds to step S209.

In step S209, it is determined whether the heater control has been continued. When the result of the determination of step S209 shows that the heater control has been continued (Yes in step S209), the processing returns to step S206, and the processes of steps S206 to S208 are repeated. On the other hand, when the heater control has been finished (No in step S209), the control flow is finished.

In the time charts of FIGS. 7A to 7F, the sensor output current Iac continuously increases with increase in the sensor temperature in a section from time t0 to time t1 as illustrated in FIG. 7F. In this section, the sensor output current Iac has not exceeded the threshold THIac. Thus, steps S206, S207 are repeated. At this time, in the sensor impedance-cut-off frequency characteristic of FIG. 3, the cut-off frequency is set to the one in the region D1 at the high frequency side.

When the sensor output current Iac exceeds the threshold THIac at the time t1, the cut-off frequency change switch SW2 is switched to an OFF state as illustrated in FIG. 7C to change the cut-off frequency to the low frequency one. At this time, in the sensor impedance-cut-off frequency characteristic of FIG. 3, the cut-off frequency makes a transition to the region D2 at the low frequency side. Accordingly, the sensor impedance-cut-off frequency characteristic is switched from the characteristic in the low temperature region (graph A) to the characteristic in the high temperature region (graph B). Further, at the time t1, the sensor temperature has reached the control target temperature as illustrated in FIG. 7B and sensor warming-up has been completed.

In a section from the time t1 to time t2, as illustrated in FIG. 7B, a state of the sensor temperature exceeding the control target temperature is maintained, and the sensor temperature starts decreasing when the engine state is switched from a normal state to a stopped state at the time t2. In a section from the time t2 to time t3, the sensor output current Iac continuously decreases with decrease in the sensor temperature as illustrated in FIG. 7F. In this section, the sensor output current Iac has not exceeded the threshold THIac. Thus, steps S206, S207 are repeated. At this time, in the sensor impedance-cut-off frequency characteristic of FIG. 3, the cut-off frequency remains in the region D2 at the low frequency side.

When the sensor output current Iac exceeds the threshold THIac at the time t3, the cut-off frequency change switch SW2 is switched to an ON state as illustrated in FIG. 7C to again change the cut-off frequency to the high frequency one. At this time, in the sensor impedance-cut-off frequency characteristic of FIG. 3, the cut-off frequency again makes a transition to the region D1 at the high frequency side.

As described above, in the second embodiment, the cut-off frequency is variable on the basis of the sensor output current Iac differently from the first embodiment. Specifically, when the sensor output current Iac is relatively small, the element temperature is determined to be relatively low, and the cut-off frequency is set to be relatively high. On the other hand, when the sensor output current Iac is relatively large, the element temperature is determined to be relatively high, and the cut-off frequency is set to be relatively low. Similarly to the sensor impedance Zac of the first embodiment, the sensor output current Iac corresponds to the high-low relation in the element temperature of the oxygen content sensor 3 and is information that appropriately reflects changes in the element temperature. Thus, the configuration of the second embodiment can also achieve an effect similar to the effect of the first embodiment.

(Modification of Second Embodiment)

A modification of the second embodiment will be described with reference to FIGS. 8A to 8F. A time charts of FIGS. 8A to 8F illustrates (a) engine state, (b) sensor temperature (an actual element temperature of the oxygen content sensor 3), (c) CUT-OFF-SW (a control signal for the cut-off frequency change switch SW2 in the applied voltage control circuit 11), (d) cut-off frequency, (e) AC voltage (AC voltage Vac) applied waveform, and (f) change in sensor output current Idc (direct current Idc) with time during the cut-off frequency switching processing.

When a sensor output current that is output from the oxygen content sensor 3 in response to an applied voltage is used as the element temperature related information as an index for switching the cut-off frequency, the direct current Idc which is output in response to the application of a DC voltage Vdc may be used instead of the alternating current Iac which is output in response to the application of the AC voltage Vac as described in the second embodiment. The direct current Idc is an index value corresponding to the oxygen content detected by the oxygen content sensor 3 as described above. The oxygen content sensor 3 can output an original direct current Idc according to a sensor gas atmosphere with activation thereof, and the direct current Idc increases as the sensor temperature increases. That is, the direct current Idc has a relationship with the element temperature of the oxygen content sensor 3. For example, as illustrated in FIGS. 8B and 8F, the amplitude of the direct current Idc increases as the element temperature increases for activation, and the maximum value of the amplitude becomes saturated (approaches a predetermined value) when the element temperature becomes a high temperature in some degree.

When the direct current Idc is used as the element temperature related information, for example, as illustrated in FIG. 8F, a predetermined threshold THIdc is set to enable the high or low of the element temperature to be determined by the relationship between a transition of the direct current Idc with time and the threshold THIdc. For example, when a vibration waveform of the direct current Idc does not intersect the threshold THIdc (in a section from time t0 to time t1 and a section from time t3 to time t4 in FIGS. 8A to 8F), it is determined that the sensor output current Idc is relatively small and the element temperature is relatively low, and the cut-off frequency is set to be relatively high. On the other hand, when the vibration waveform of the direct current Idc intersects the threshold THIdc (in a section from time t1 to time t2 in FIGS. 8A to 8F), it is determined that the sensor output current Idc is relatively large and the element temperature is relatively high, and the cut-off frequency is set to be relatively low. The "state of the vibration waveform of the direct current Idc intersecting the threshold THIdc" can be determined, for example, when a state of the maximum value of the amplitude of the direct current Idc being larger than the threshold THIdc continues for a predetermined time or more.

(Third Embodiment)

Figure 9:
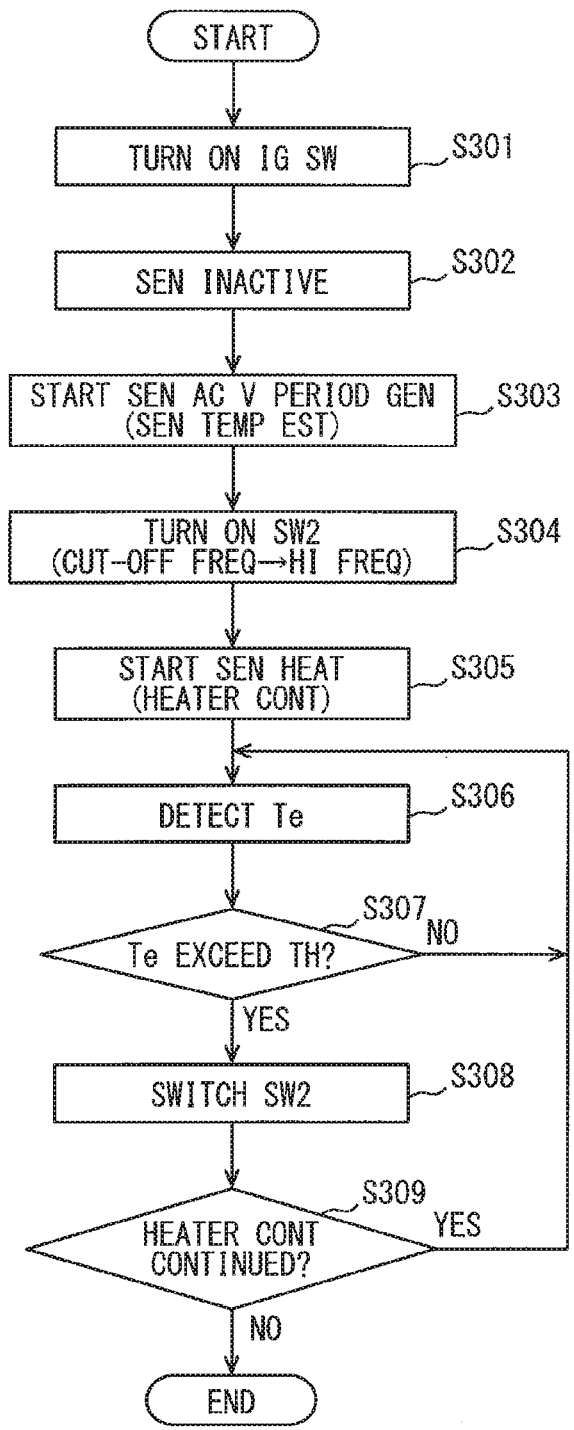
FIG. 9 is a flow chart illustrating cut-off frequency switching processing in a third embodiment.

Next, a third embodiment will be described with reference to FIGS. 9 and 10A to 10F. As illustrated in FIG. 9, the third embodiment differs from the first and second embodiments in that an exhaust gas temperature Te inside the exhaust pipe 2 (sensor atmospheric gas temperature) is used as the element temperature related information related to the element temperature of the oxygen content sensor 3 and the cut-off frequency is variable on the basis of the exhaust gas temperature Te.

As illustrated in FIG. 1, the exhaust gas temperature Te is the temperature of an exhaust gas (gas to be detected) inside the exhaust pipe 2, the oxygen content of the exhaust gas being detected by the oxygen content sensor 3, in other words, the temperature of an atmospheric gas inside a space (exhaust pipe 2) in which the oxygen content sensor 3 is placed. As illustrated in FIGS. 10B and 10F, the large-small relation in the exhaust gas temperature Te also corresponds to the high-low relation in the element temperature of the oxygen content sensor 3 similarly to the sensor impedance Zac.

Processing of switching the cut-off frequency of the applied voltage control circuit 11 in the third embodiment will be described with reference to a flow chart of FIG. 9 and time charts of FIGS. 10A to 10F. A series of processes in the time chart of FIG. 9 is performed by the sensor control device 10 when the engine 1 is in an operating state. The time charts of FIGS. 10A to 10F illustrates (a) engine state, (b) sensor temperature (an actual element temperature of the oxygen content sensor 3), (c) CUT-OFF-SW (a control signal for the cut-off frequency change switch SW2 in the applied voltage control circuit 11), (d) cut-off frequency, (e) AC voltage (AC voltage Vac) applied waveform, and (f) change in exhaust gas temperature Te with time during the cut-off frequency switching processing. Hereinbelow, description will be made following the flow chart of FIG. 9 and referring to the time charts of FIGS. 10A to 10. Since processes of steps S301 to S305 are respectively similar to the processes of steps S101 to S105 of FIG. 4, description thereof will be omitted.

In step S306, the exhaust gas temperature Te is detected. As illustrated in FIG. 1, the microcomputer 13 acquires information about the exhaust gas temperature Te from the exhaust gas temperature sensor 6. After completion of the process of step S306, the processing proceeds to step S307.

In step S307, it is determined whether the exhaust gas temperature Te has exceeded a threshold THt. When the result of the determination of step S307 shows that the exhaust gas temperature Te has not exceeded the threshold THt (No in step S307), the processing returns to step S306. When the exhaust gas temperature Te has exceeded the threshold (Yes in step S307), the processing proceeds to step S308.

Since the exhaust gas temperature Te has exceeded the threshold in step S307, the cut-off frequency change switch SW2 is switched in step S308. Specifically, the cut-off frequency change switch SW2 is switched to an OFF state when in an ON state or switched to an ON state when in an OFF state. After completion of the process of step S308, the processing proceeds to step S309.

In step S309, it is determined whether the heater control has been continued. When the result of the determination of step S309 shows that the heater control has been continued (Yes in step S309), the processing returns to step S306, and the processes of steps S306 to S308 are repeated. On the other hand, when the heater control has been finished (No in step S309), the control flow is finished.

In the time charts of FIGS. 10A to 10F, the exhaust gas temperature Te continuously increases with increase in the sensor temperature in a section from time t0 to time t1 as illustrated in FIG. 10F. In this section, the exhaust gas temperature Te has not exceeded the threshold THt. Thus, steps S306, S307 are repeated. At this time, in the sensor impedance-cut-off frequency characteristic of FIG. 3, the cut-off frequency is set to the one in the region D1 at the high frequency side.

When the exhaust gas temperature Te exceeds the threshold THt at the time t1, the cut-off frequency change switch SW2 is switched to an OFF state as illustrated in FIG. 10C to change the cut-off frequency to the low frequency one. At this time, in the sensor impedance-cut-off frequency characteristic of FIG. 3, the cut-off frequency makes a transition to the region D2 at the low frequency side. Accordingly, the sensor impedance-cut-off frequency characteristic is switched from the characteristic in the low temperature region (graph A) to the characteristic in the high temperature region (graph B), Further, at the time t1, the sensor temperature has reached the control target temperature as illustrated in FIG. 10B and sensor warming-up has been completed.

In a section from the time t1 to time t2, as illustrated in FIG. 10B, a state of the sensor temperature exceeding the control target temperature is maintained, and the sensor temperature starts decreasing when the engine state is switched from a normal state to a stopped state at the time t2. In a section from the time t2 to time t3, the exhaust gas temperature Te continuously decreases with decrease in the sensor temperature as illustrated in FIG. 10F. In this section, the exhaust gas temperature Te has not exceeded the threshold THt. Thus, steps S306, S307 are repeated. At this time, in the sensor impedance-cut-off frequency characteristic of FIG. 3, the cut-off frequency remains in the region D2 at the low frequency side.

When the exhaust gas temperature Te exceeds the threshold THt at the time t3, the cut-off frequency change switch SW2 is switched to an ON state as illustrated in FIG. 10C to again change the cut-off frequency to the high frequency one. At this time, in the sensor impedance-cut-off frequency characteristic of FIG. 3, the cut-off frequency again makes a transition to the region D1 at the high frequency side.

As described above, in the third embodiment, the cut-off frequency is variable on the basis of the exhaust gas temperature Te differently from the first embodiment. Specifically, when the exhaust gas temperature Te is relatively low, the element temperature is determined to be relatively low, and the cut-off frequency is set to be relatively high. On the other hand, when the exhaust gas temperature Te is relatively high, the element temperature is determined to be relatively high, and the cut-off frequency is set to be relatively low. Similarly to the sensor impedance Zac of the first embodiment, the exhaust gas temperature Te corresponds to the high-low relation in the element temperature of the oxygen content sensor 3 and is information that appropriately reflects changes in the element temperature. Thus, the configuration of the third embodiment can also achieve an effect similar to the effect of the first embodiment.

In the third embodiment, there has been described, as an example, the configuration that uses the exhaust gas temperature Te as the element temperature related information used for the determination of switching of the cut-off frequency. Alternatively, any configuration that uses the temperature of an atmospheric gas in a space in which a control target sensor is placed may be employed. For example, when the control target sensor is placed in an intake pipe, an intake-air temperature may be used. Alternatively, a temperature at a position away from the sensor may be used as long as whether the temperature of an atmospheric gas in a space in which the control target sensor is placed is low or high can be estimated.

(Fourth Embodiment)

Figure 11:
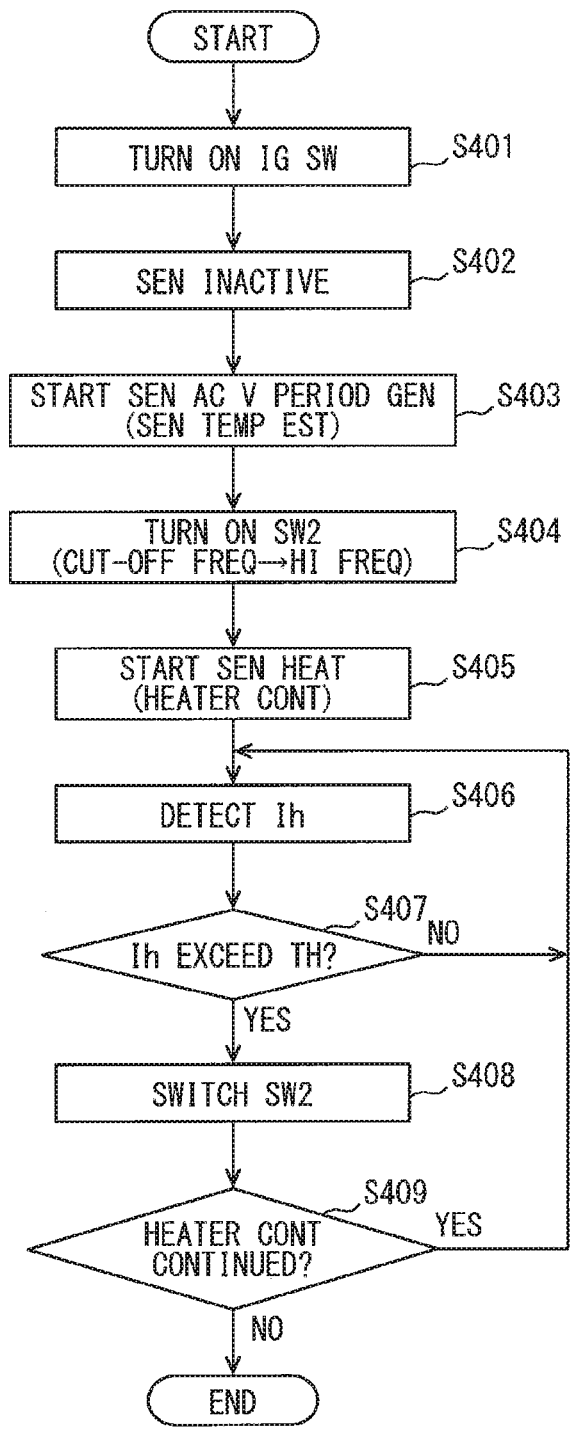
FIG. 11 is a flow chart illustrating cut-off frequency switching processing in a fourth embodiment.

Next, a fourth embodiment will be described with reference to FIGS. 11 and 12A to 12F. As illustrated in FIG. 11, the fourth embodiment differs from the first embodiment in that a heater current Ih is used as the element temperature related information related to the element temperature of the oxygen content sensor 3 and the cut-off frequency is variable on the basis of the heater current Ih.

The heater current Ih flows inside the heater 5 when the heater 5 heats the sensor element 4 of the oxygen content sensor 3. In temperature raising control for the element temperature, generally, as the element temperature is separated farther from a set temperature toward the low temperature side, the duty factor of the heater 5 (heater duty factor) is controlled to be higher to increase the heater current Ih. On the other hand, as the element temperature increases and comes closer to the set temperature, the duty factor of the heater 5 is controlled to be lower to reduce the heater current Ih. Thus, as illustrated in FIGS. 12B and 12F, the large-small relation in the heater current Ih also corresponds to the high-low relation in the element temperature of the oxygen content sensor 3 similarly to the sensor impedance Zac.

Processing of switching the cut-off frequency of the applied voltage control circuit 11 in the fourth embodiment will be described with reference to a flow chart of FIG. 11 and time charts of FIGS. 12A to 12F. A series of processes in the time chart of FIG. 11 is performed by the sensor control device 10 when the engine 1 is in an operating state. The time charts of FIGS. 12A to 12F illustrates (a) engine state, (b) sensor temperature (an actual element temperature of the oxygen content sensor 3), (c) CUT-OFF-SW (a control signal for the cut-off frequency change switch SW2 in the applied voltage control circuit 11), (d) cut-off frequency, (e) AC voltage (AC voltage Vac) applied waveform, and (f) change in heater current Ih with time during the cut-off frequency switching processing. Hereinbelow, description will be made following the flow chart of FIG. 11 and referring to the time charts of FIGS. 12A to 12F. Since processes of steps S401 to S405 are respectively similar to the processes of steps S101 to S105 of FIG. 4, description thereof will be omitted.

In step S406, the heater current Ih is detected. The microcomputer 13 may calculate the heater current from information about the duty factor of the heater 5 by the heater control circuit 12 or may directly acquire information about a current value from the heater 5. After completion of the process of step S406, the processing proceeds to step S407.

In step S407, it is determined whether the heater current Ih has exceeded a threshold THh. When the result of the determination of step S407 shows that the heater current Ih has not exceeded the threshold THh (No in step S407), the processing returns to step S406. When the heater current Ih has exceeded the threshold (Yes in step S407), the processing proceeds to step S408.

Since the heater current Ih has exceeded the threshold in step S407, the cut-off frequency change switch SW2 is switched in step S408. Specifically, the cut-off frequency change switch SW2 is switched to an OFF state when in an ON state or switched to an ON state when in an OFF state. After completion of the process of step S408, the processing proceeds to step S409.

In step S409, it is determined whether the heater control has been continued. When the result of the determination of step S409 shows that the heater control has been continued (Yes in step S409), the processing returns to step S406, and the processes of steps S406 to S408 are repeated. On the other hand, when the heater control has been finished (No in step S409), the control flow is finished.

In the time charts of FIGS. 12A to 12F, the heater current Ih continuously decreases with increase in the sensor temperature in a section from time t0 to time t1 as illustrated in FIG. 12F. In this section, the heater current Ih has not exceeded the threshold THh. Thus, steps S406, S407 are repeated. At this time, in the sensor impedance-cut-off frequency characteristic of FIG. 3, the cut-off frequency is set to the one in the region D1 at the high frequency side.

When the heater current Ih exceeds the threshold THh at the time t1, the cut-off frequency change switch SW2 is switched to an OFF state as illustrated in FIG. 12C to change the cut-off frequency to the low frequency one. At this time, in the sensor impedance-cut-off frequency characteristic of FIG. 3, the cut-off frequency makes a transition to the region D2 at the low frequency side. Accordingly, the sensor impedance-cut-off frequency characteristic is switched from the characteristic in the low temperature region (graph A) to the characteristic in the high temperature region (graph B). Further, at the time t1, the sensor temperature has reached the control target temperature as illustrated in FIG. 12B and sensor warming-up has been completed.

In a section from the time t1 to time t2, as illustrated in FIG. 12B, a state of the sensor temperature exceeding the control target temperature is maintained, and the sensor temperature starts decreasing when the engine state is switched from a normal state to a stopped state at the time t2. In a section from the time t2 to time t3, the heater current Ih continuously increases with decrease in the sensor temperature as illustrated in FIG. 12F. In this section, the heater current Ih has not exceeded the threshold THh. Thus, steps S406, S407 are repeated. At this time, in the sensor impedance-cut-off frequency characteristic of FIG. 3, the cut-off frequency remains in the region D2 at the low frequency side.

When the heater current Ih exceeds the threshold THh at the time t3, the cut-off frequency change switch SW2 is switched to an ON state as illustrated in FIG. 12C to again change the cut-off frequency to the high frequency one. At this time, in the sensor impedance-cut-off frequency characteristic of FIG. 3, the cut-off frequency again makes a transition to the region D1 at the high frequency side.

As described above, in the fourth embodiment, the cut-off frequency is variable on the basis of the heater current Ih differently from the first embodiment. Specifically, when the heater current Ih is relatively large, the element temperature is determined to be relatively low, and the cut-off frequency is set to be relatively high. On the other hand, when the heater current Ih is relatively small, the element temperature is determined to be relatively high, and the cut-off frequency is set to be relatively low. Similarly to the sensor impedance Zac of the first embodiment, the heater current Ih corresponds to the high-low relation in the element temperature of the oxygen content sensor 3 and is information that appropriately reflects changes in the element temperature. Thus, the configuration of the fourth embodiment can also achieve an effect similar to the effect of the first embodiment.

When the heater current Ih is used as the element temperature related information, a characteristic of the heater current Ih varying corresponding to the size of the resistance inside the heater 5 (heater resistance) regardless of the heater duty factor may also be used. The heater current Ih has as characteristic of varying with increase in the temperature of the heater 5 (heater temperature) regardless of the heater duty factor, that is, even when the heater duty factor remains constant. Generally, when the heater temperature is low, the heater resistance is small and the heater current Ih is thus relatively large. On the other hand, when the heater temperature is high, the heater resistance is large and the heater current Ih is thus relatively small. When the cut-off frequency is made variable using this characteristic, the cut-off frequency may be set regardless of the duty factor of the heater 5 in the following manner. When the heater resistance is relatively small and the heater current Ih is relatively large, the element temperature is determined to be relatively low and the cut-off frequency is set to be relatively high. On the other hand, when the heater resistance is relatively large and the heater current Ih is relatively small, the element temperature is determined to be relatively high and the cut-off frequency is set to be relatively low.

Further, the switching of the cut-off frequency based on the heater current Ih may be set opposite to that in the fourth embodiment depending on the characteristic of the oxygen content sensor 3 as a control target. That is, when the heater current Ih is employed as the element temperature related information, the switching of the cut-off frequency may be performed in the following manner. When the heater current Ih is relatively small, the element temperature is determined to be relatively low and the cut-off frequency is set to be relatively high. On the other hand, when the heater current Ih is relatively large, the element temperature is determined to be relatively high and the cut-off frequency is set to be relatively low.

(Fifth Embodiment)

Figure 13:
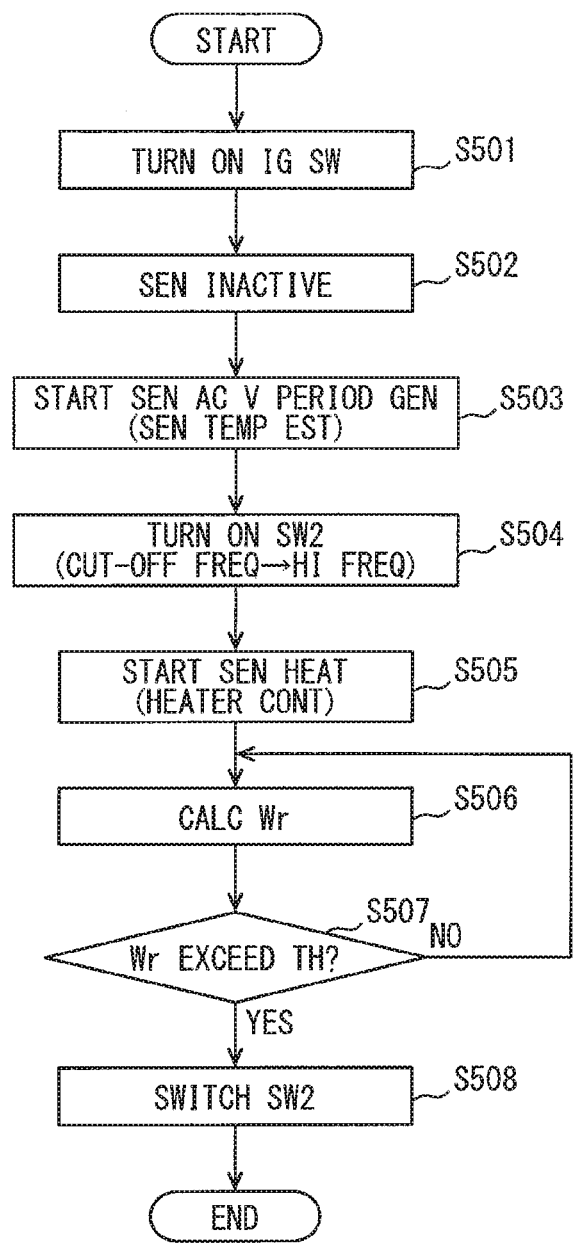
FIG. 13 is a flow chart illustrating cut-off frequency switching processing in a fifth embodiment.

Next, a fifth embodiment will be described with reference to FIGS. 13 and 14A to 14F. As illustrated in FIG. 13, the fifth embodiment differs from the first embodiment in that a sensor heating power Wr is used as the element temperature related information related to the element temperature of the oxygen content sensor 3 and the cut-off frequency is variable on the basis of the sensor heating power Wr.

The sensor heating power Wr is the amount of power consumption in the heater 5 when the heater 5 heats the sensor element 4 of the oxygen content sensor 3. The sensor heating power Wr increases in an integrated manner during the execution of temperature raising control for the element temperature of the oxygen content sensor 3. As illustrated in FIGS. 14B and 14F, an increasing tendency of the sensor heating power Wr corresponds to a rise in the sensor temperature by the temperature raising control.

Processing of switching the cut-off frequency of the applied voltage control circuit 11 in the fifth embodiment will be described with reference to a flow chart of FIG. 13 and time charts of FIGS. 14A to 14F. A series of processes in the time chart of FIG. 13 is performed by the sensor control device 10 when the engine 1 is in an operating state. The time charts of FIGS. 14A to 14F illustrates (a) engine state, (b) sensor temperature (an actual element temperature of the oxygen content sensor 3), (c) CUT-OFF-SW (a control signal for the cut-off frequency change switch SW2 in the applied voltage control circuit 11), (d) cut-off frequency, (e) AC voltage (AC voltage Vac) applied waveform, and (f) change in sensor heating power Wr with time during the cut-off frequency switching processing. Hereinbelow, description will be made following the flow chart of FIG. 13 and referring to the time charts of FIGS. 14A to 14F. Since processes of steps S501 to S505 are respectively similar to the processes of steps S101 to S105 of FIG. 4, description thereof will be omitted.

In step S506, the sensor heating power Wr is calculated. The microcomputer 13 may calculate the sensor heating power Wr from information about the duty factor of the heater 5 by the heater control circuit 12 or may directly acquire information about the power consumption amount from the heater 5. After completion of the process of step S506, the processing proceeds to step S507.

In step S507, it is determined whether the sensor heating power Wr has exceeded a threshold THw. When the result of the determination of step S507 shows that the sensor heating power Wr has not exceeded the threshold THw (No in step S507), the processing returns to step S506. When the sensor heating power Wr has exceeded the threshold (Yes in step S507), the processing proceeds to step S508.

Since the sensor heating power Wr has exceeded the threshold in step S507, the cut-off frequency change switch SW2 is switched to an OFF state in step S508. After completion of the process of step S508, the control flow is finished.

In the time charts of FIGS. 14A to 14F, the sensor heating power Wr continuously increases with increase in the sensor temperature in a section from time t0 to time t1 as illustrated in FIG. 14F. In this section, the sensor heating power Wr has not exceeded the threshold THw. Thus, steps S506, S507 are repeated. At this time, in the sensor impedance-cut-off frequency characteristic of FIG. 3, the cut-off frequency is set to the one in the region D1 at the high frequency side.

When the sensor heating power Wr exceeds the threshold THw at the time t1, the cut-off frequency change switch SW2 is switched to an OFF state as illustrated in FIG. 14C to change the cut-off frequency to the low frequency one. At this time, in the sensor impedance-cut-off frequency characteristic of FIG. 3, the cut-off frequency makes a transition to the region D2 at the low frequency side. Accordingly, the sensor impedance-cut-off frequency characteristic is switched from the characteristic in the low temperature region (graph A) to the characteristic in the high temperature region (graph B).

As described above, in the fifth embodiment, the cut-off frequency is variable on the basis of the sensor heating power Wr differently from the first embodiment. Specifically, when the sensor heating power Wr is relatively small, the element temperature is determined to be relatively low, and the cut-off frequency is set to be relatively high. On the other hand, when the sensor heating power Wr is relatively large, the element temperature is determined to be relatively high, and the cut-off frequency is set to be relatively low. Similarly to the sensor impedance Zac of the first embodiment, the sensor heating power Wr corresponds to the high-low relation in the element temperature of the oxygen content sensor 3 and is information that appropriately reflects changes in the element temperature. Thus, the configuration of the fifth embodiment can also achieve an effect similar to the effect of the first embodiment.

In the fifth embodiment, there has been described, as an example, the configuration that uses the sensor heating power Wr as the element temperature related information. Alternatively, a sensor heating time may be used. The sensor heating time is the amount of time elapsed when the heater 5 heats the sensor element 4 of the oxygen content sensor 3. The sensor heating time increases in an integrated manner during the execution of the temperature raising control for the element temperature of the oxygen content sensor 3 similarly to the sensor heating power Wr, and makes a transition with time similarly to the sensor heating power Wr in FIG. 14F. That is, when the sensor heating time is relatively short, the element temperature may be determined to be relatively low and the cut-off frequency may be set to be relatively high. On the other hand, when the sensor heating time is relatively long, the element temperature may be determined to be relatively high and the cut-off frequency may be set to be relatively low.

The embodiments of the present disclosure have been described above with reference to the specific examples. However, the present disclosure is not limited to these specific examples. That is, embodiments obtained by appropriately modifying these specific examples by those skilled in the art are also included in the scope of the disclosure as long as they have the features of the present disclosure. For example, each element provided in each of the specific examples, and the arrangement, material, condition, shape and size thereof are not limited to the illustrated ones, and may be appropriately modified. The elements of the above embodiments may be combined in a technically possible manner and combinations of these elements are also included in the scope of the disclosure as long as they have the features of the present disclosure.

In the above embodiments, the oxygen content sensor 3 has been described as an example of the control target of the sensor control device 10. The control target may be any sensor that allows a current Idc corresponding to the oxygen amount to flow therethrough by the application of the DC voltage Vdc and is capable of detecting the oxygen amount. Thus, a sensor of another form such as an air-fuel ratio sensor may be applied.

In the above embodiments, the applied voltage control circuit 11 has been described as an example of the applied voltage control device which controls the AC voltage Vac applied to the oxygen content sensor 3. Alternatively, another circuit configuration that is capable of exhibiting a similar function may be employed, or a similar function may be achieved by software.

In the above embodiments, there has been described, as an example, the configuration that switches the cut-off frequency between two stages according to the element temperature of the oxygen content sensor 3. Alternatively, the cut-off frequency may be switched between three stages.

In the above embodiments, there has been described, as an example, the configuration that changes the cut-off frequency by switching energization to the resistor R7 in the filter circuit 16 in the applied voltage control circuit 11. Alternatively, the cut-off frequency may be changed by another configuration, for example, in such a manner that the filter circuit has a plurality of capacitors and the capacitors may be switched by, for example, a switch.

In the above embodiments, there has been described, as an example, the configuration that acquires a state of the element temperature on the basis of the element temperature related information related to the element temperature of the oxygen content sensor 3 to switch the cut-off frequency. Alternatively, the element temperature may be directly measured from the oxygen content sensor 3, and the cut-off frequency may be switched on the basis of the measured element temperature.

It is noted that a flowchart or the processing of the flowchart in the present application includes sections (also referred to as steps), each of which is represented, for instance, as S101. Further, each section can be divided into several sub-sections while several sections can be combined into a single section. Furthermore, each of thus configured sections can be also referred to as a device, module, or means.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. An applied voltage control device for a sensor, in which a direct current corresponding to an oxygen amount flows when a DC voltage is applied to the sensor, and an alternating current corresponding to a sensor impedance flows when an AC voltage is applied to the sensor, the applied voltage control device comprising:
   a heater that heats the sensor to control the temperature of the sensor to be a predetermined set temperature; and
   a filtering unit configured to switch between different cut-off frequencies to selectively set a cut-off frequency of the AC voltage applied to the sensor to be variable, wherein
   the filtering unit is configured to set the cut-off frequency to be variable based on element temperature related information related to an element temperature of the sensor, the element temperature related information includes a heater current when the heater heats the sensor, and
   the filtering unit is configured to selectively set the cut-off frequency to be high in response to a determination that the heater current is large and selectively set the cut-off frequency to be low in response to a determination that the heater current is small.

2. The applied voltage control device according to claim 1, wherein:
   the filtering unit sets the cut-off frequency to be high when the element temperature is low, and sets the cut-off frequency to be low when the element temperature is high, based on element temperature related information.

3. An applied voltage control device for a sensor, in which a direct current corresponding to an oxygen amount flows when a DC voltage is applied to the sensor, and an alternating current corresponding to a sensor impedance flows when an AC voltage is applied to the sensor, the applied voltage control device comprising:
   a heater that heats the sensor to control the temperature of the sensor to be a predetermined set temperature; and
   a filtering unit configured to switch between different cut-off frequencies to selectively set a cut-off frequency of the AC voltage applied to the sensor to be variable, wherein
   the filtering unit is configured to set the cut-off frequency to be variable based on element temperature related information related to an element temperature of the sensor, the element temperature related information includes a heater current when the heater heats the sensor, and
   the filtering unit is configured to selectively set the cut-off frequency to be high in response to a determination that the heater current is small and selectively set the cut-off frequency to be low in response to a determination that the heater current is large.

4. An applied voltage control device for a sensor, in which a direct current corresponding to an oxygen amount flows when a DC voltage is applied to the sensor, and an alternating current corresponding to a sensor impedance flows when an AC voltage is applied to the sensor, the applied voltage control device comprising:
   a heater that heats the sensor to control the temperature of the sensor to be a predetermined set temperature; and
   a filtering unit configured to switch between different cut-off frequencies to selectively set a cut-off frequency of the AC voltage applied to the sensor to be variable, wherein
   the filtering unit is configured to set the cut-off frequency to be variable based on element temperature related information related to an element temperature of the sensor, the element temperature related information includes a sensor heating power that is an amount of power consumption when the heater heats the sensor, and
   the filtering unit is configured to selectively set the cut-off frequency to be high in response to a determination that the sensor heating power is small and selectively set the cut-off frequency to be low in response to a determination that the sensor heating power is large.

5. An applied voltage control device for a sensor, in which a direct current corresponding to an oxygen amount flows when a DC voltage is applied to the sensor, and an alternating current corresponding to a sensor impedance flows when an AC voltage is applied to the sensor, the applied voltage control device comprising:
   a heater that heats the sensor to control the temperature of the sensor to be a predetermined set temperature; and
   a filtering unit configured to switch between different cut-off frequencies to selectively set a cut-off frequency of the AC voltage applied to the sensor to be variable, wherein
   the filtering unit is configured to set the cut-off frequency to be variable based on element temperature related information related to an element temperature of the sensor, the element temperature related information includes a sensor heating time that is an amount of elapsed time when the heater heats the sensor, and
   the filtering unit is configured to selectively set the cut-off frequency to be high in response to a determination that the sensor heating time is short, and selectively set the cut-off frequency to be low in response to a determination that the sensor heating time is long.

6. The applied voltage control device according to claim 3, wherein:
   the filtering unit sets the cut-off frequency to be high when the element temperature is low, and sets the cut-off frequency to be low when the element temperature is high, based on element temperature related information.

7. The applied voltage control device according to claim 4, wherein:
   the filtering unit sets the cut-off frequency to be high when the element temperature is low, and sets the cut-off frequency to be low when the element temperature is high, based on element temperature related information.

8. The applied voltage control device according to claim 5, wherein:
   the filtering unit sets the cut-off frequency to be high when the element temperature is low, and sets the cut-off frequency to be low when the element temperature is high, based on element temperature related information.

9. The applied voltage control device according to claim 4, further comprising
   a microcomputer configured to output a command signal to the filtering unit to control the filtering unit to selectively set the cut-off frequency in response to a determination regarding the element temperature related information.

10. The applied voltage control device according to claim 5, further comprising
    a microcomputer configured to output a command signal to the filtering unit to control the filtering unit to selectively set the cut-off frequency in response to a determination regarding the element temperature related information.

11. The applied voltage control device according to claim 4, wherein
    the microcomputer is configured to output a command signal to the filtering unit to control the filtering unit to selectively set the cut-off frequency to switch between different detection states that each have a predetermined variation in the sensor impedance.

12. The applied voltage control device according to claim 5, wherein
    the microcomputer is configured to output a command signal to the filtering unit to control the filtering unit to selectively set the cut-off frequency to switch between different detection states that each have a predetermined variation in the sensor impedance.

* * * * *